United States Patent
Gallo, Sr. et al.

(10) Patent No.: US 8,986,299 B2
(45) Date of Patent: Mar. 24, 2015

(54) ABLATOR WITH SCALLOPED ELECTRODE AND SWAGED TUBE

(75) Inventors: David P. Gallo, Sr., Naples, FL (US); Randall L. Hacker, Naples, FL (US); Terrance J. McLaughlin, Naples, FL (US); Christine A. Bickenbach, Naples, FL (US)

(73) Assignee: Arthrex, Inc., Naples, FL (US)

( * ) Notice: Subject to any disclaimer, the term of this patent is extended or adjusted under 35 U.S.C. 154(b) by 1038 days.

(21) Appl. No.: 12/639,644

(22) Filed: Dec. 16, 2009

(65) Prior Publication Data
US 2010/0152729 A1 Jun. 17, 2010

Related U.S. Application Data

(60) Provisional application No. 61/138,039, filed on Dec. 16, 2008.

(51) Int. Cl.
*A61B 18/14* (2006.01)
*A61B 18/00* (2006.01)

(52) U.S. Cl.
CPC ..... *A61B 18/148* (2013.01); *A61B 2018/00083* (2013.01); *A61B 2018/1472* (2013.01)
USPC .............................. 606/41; 606/49

(58) Field of Classification Search
USPC .............................. 606/41, 45–50
See application file for complete search history.

(56) References Cited

U.S. PATENT DOCUMENTS

| 6,142,996 | A | 11/2000 | Mirhashemi et al. | |
|---|---|---|---|---|
| 6,379,350 | B1 * | 4/2002 | Sharkey et al. | 606/41 |
| 7,150,746 | B2 * | 12/2006 | DeCesare et al. | 606/41 |
| 7,276,063 | B2 * | 10/2007 | Davison et al. | 606/41 |
| 7,481,807 | B2 * | 1/2009 | Knudsen et al. | 606/41 |
| 2004/0030330 | A1 * | 2/2004 | Brassell et al. | 606/41 |
| 2004/0054366 | A1 * | 3/2004 | Davison et al. | 606/39 |
| 2004/0116793 | A1 | 6/2004 | Taimisto et al. | |
| 2005/0277915 | A1 * | 12/2005 | DeCesare et al. | 606/41 |
| 2006/0259031 | A1 * | 11/2006 | Carmel et al. | 606/41 |

FOREIGN PATENT DOCUMENTS

| EP | 1 797 839 A1 | 6/2007 |
|---|---|---|
| WO | WO 03/068095 A1 | 8/2003 |
| WO | WO 2005/112814 A2 | 12/2005 |

\* cited by examiner

*Primary Examiner* — Michael Peffley
(74) *Attorney, Agent, or Firm* — Dickstein Shapiro LLP

(57) ABSTRACT

A high efficiency electrosurgical electrode with an advanced electrically conductive tip and advanced design tube, and a method of conducting an electrosurgical procedure with such electrode. The tube design is provided with a swaged one-piece metal tube that fits in small cannulas (as small as a 5.5 mm cannula). The electrode has a scalloped configuration that provides decreased surface area with more edges. The handle is provided with an ergonomic design that utilizes a bend with a cut at the end of the tube (for example, a 30 degree bend with a 15 degree cut).

23 Claims, 26 Drawing Sheets

Detail A

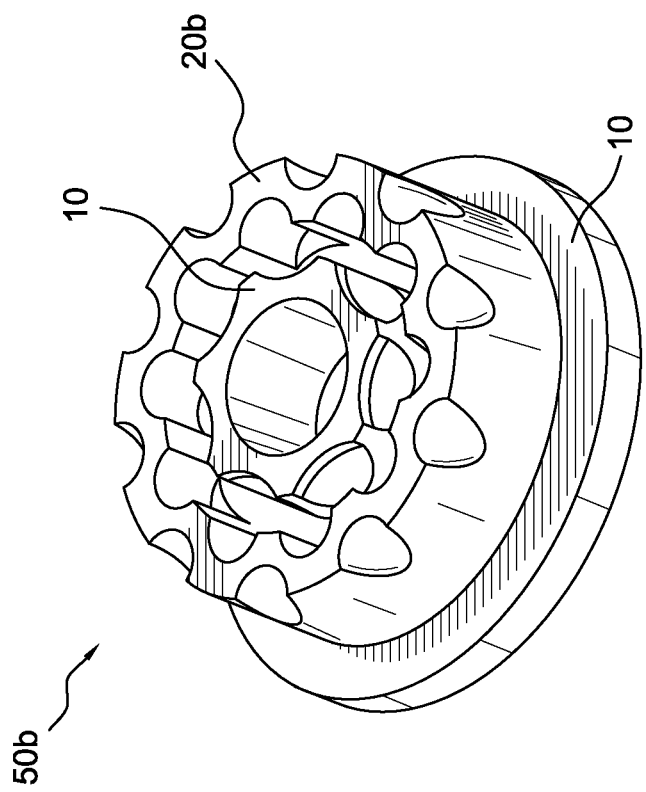
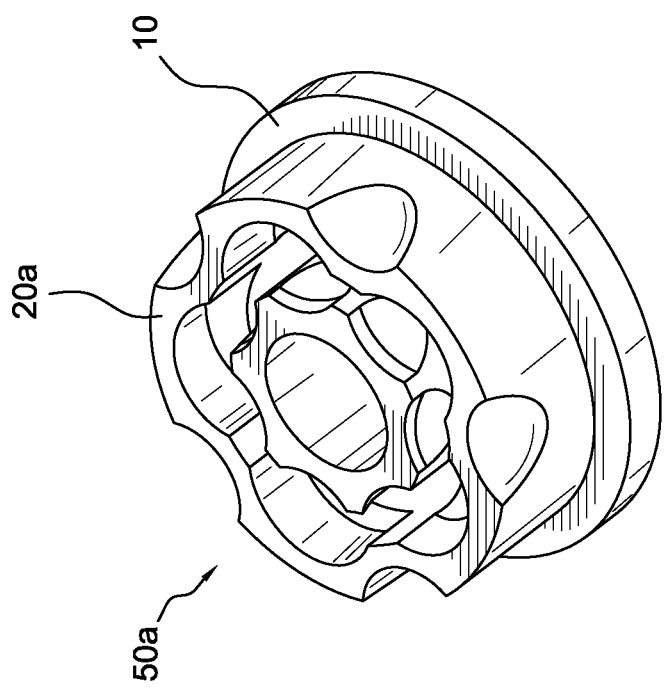
FIG. 1(a)
FIG. 1(b)

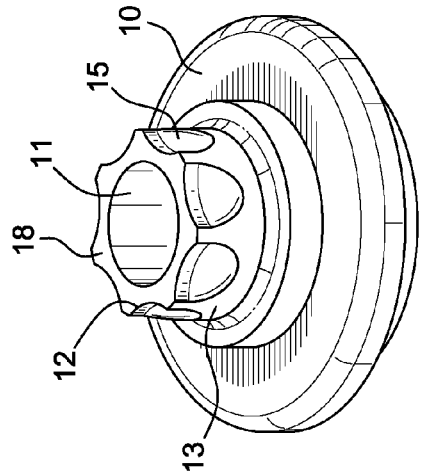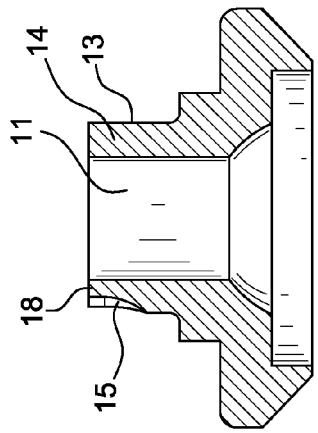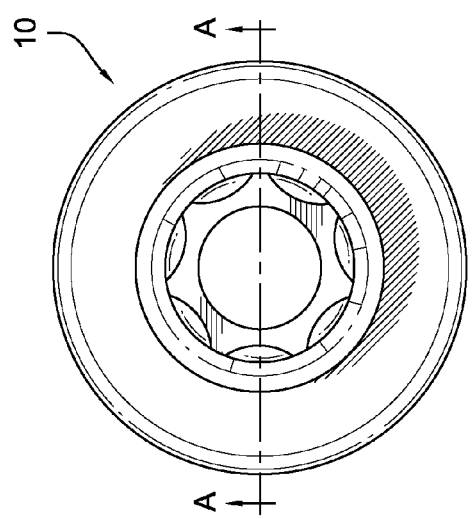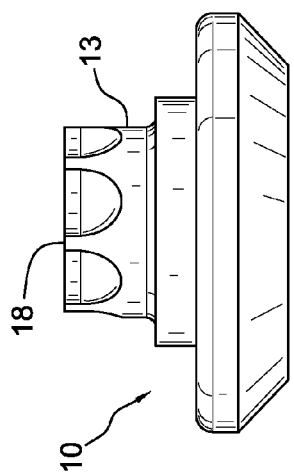
FIG. 2(a)
FIG. 2(b)
FIG. 2(c)
FIG. 2(d) Section A-A Section A-A Section A-A Section A-A

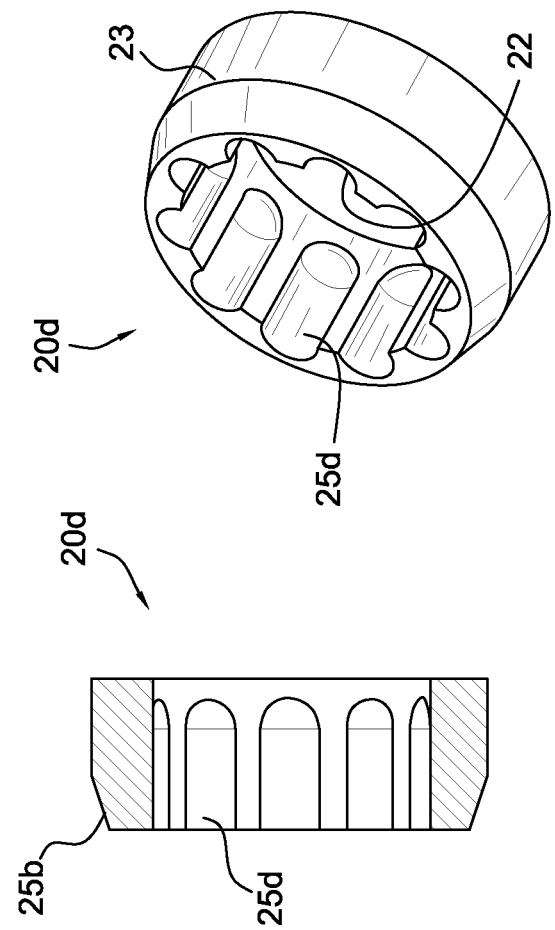
FIG. 6(c)
FIG. 6(b)
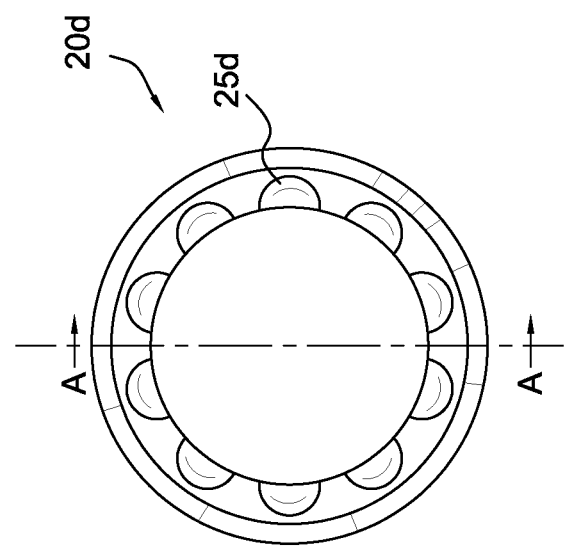
FIG. 6(a)

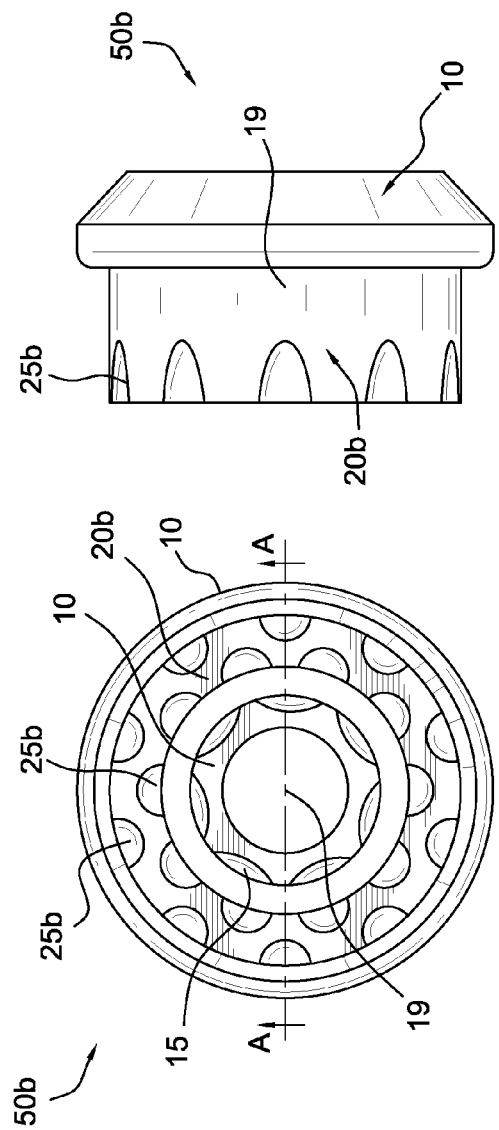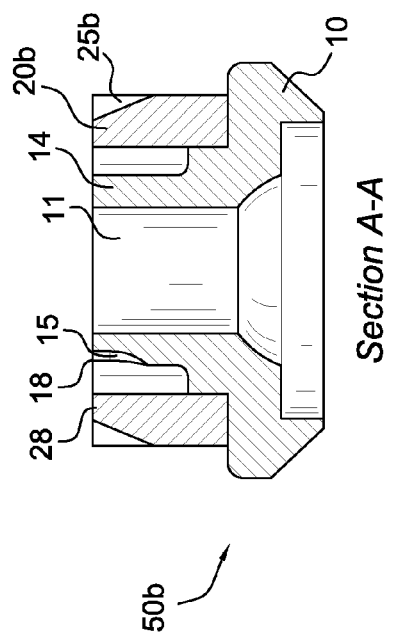

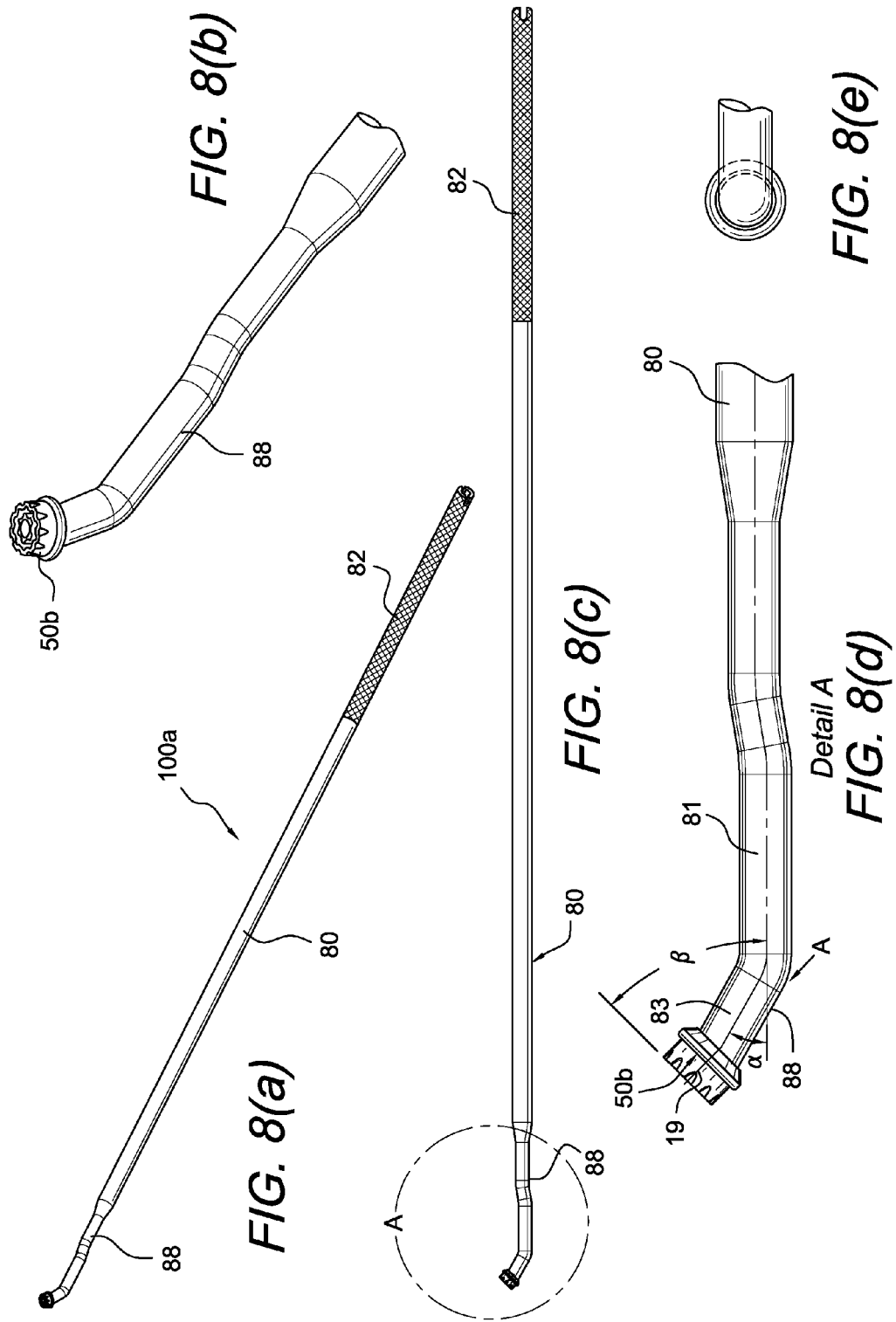

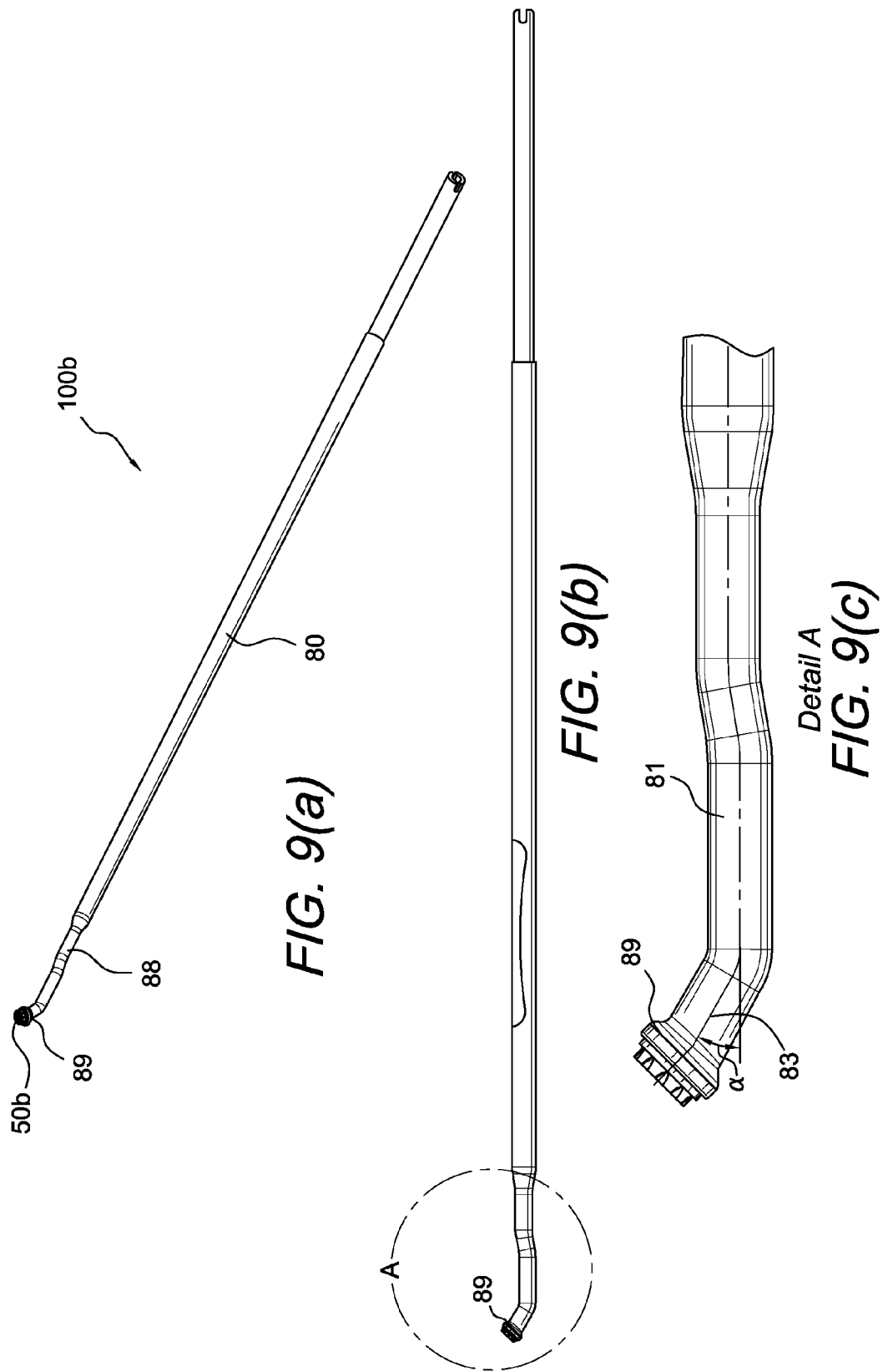

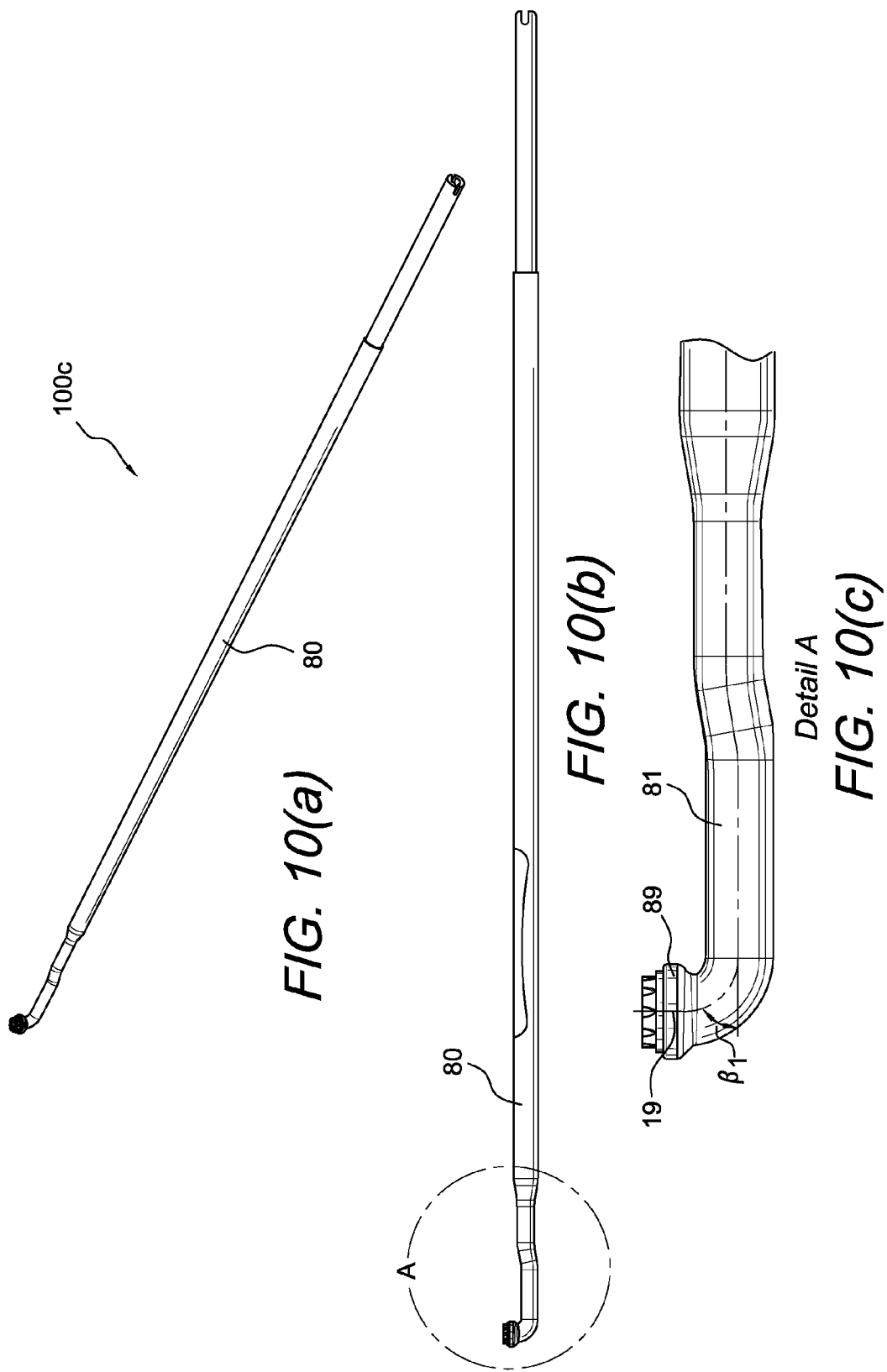

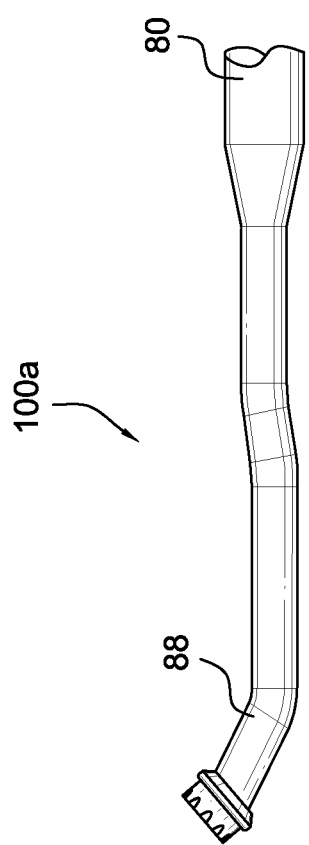
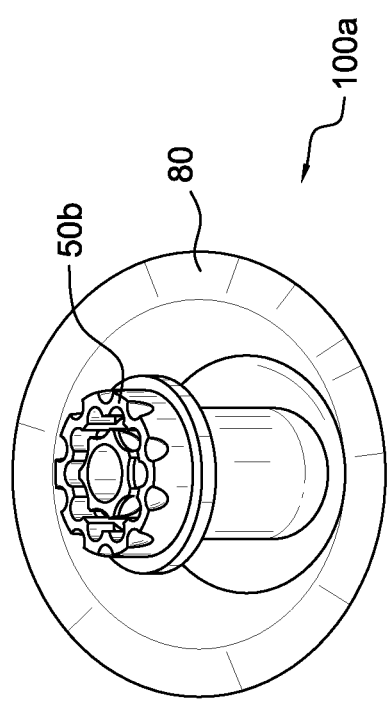
FIG. 11(a)
FIG. 11(b)

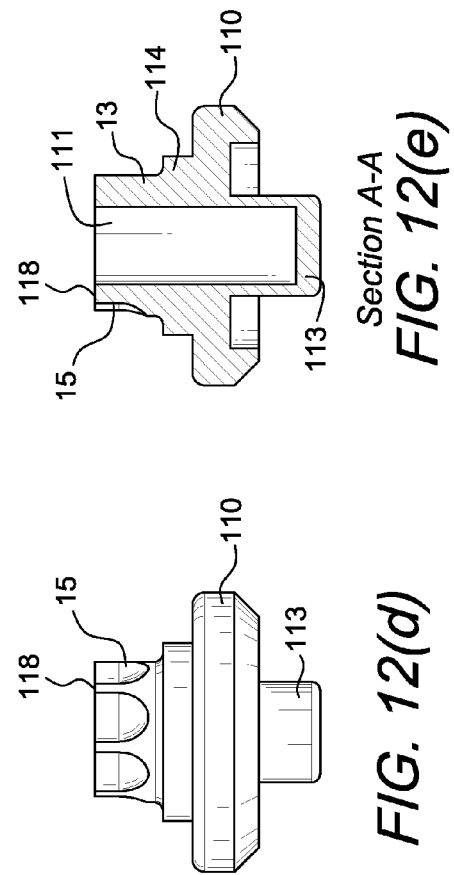
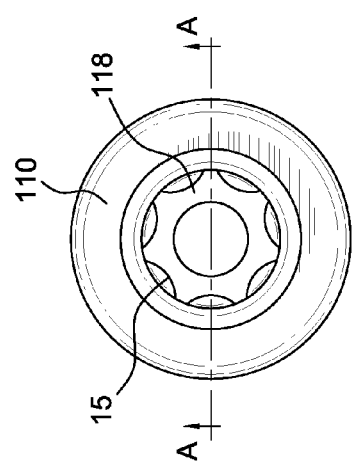
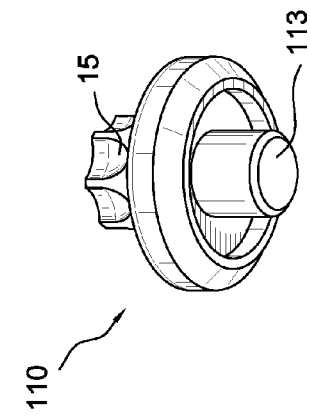
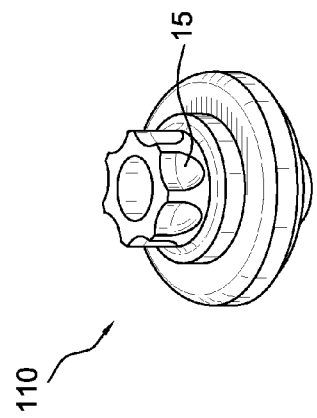

Section A-A

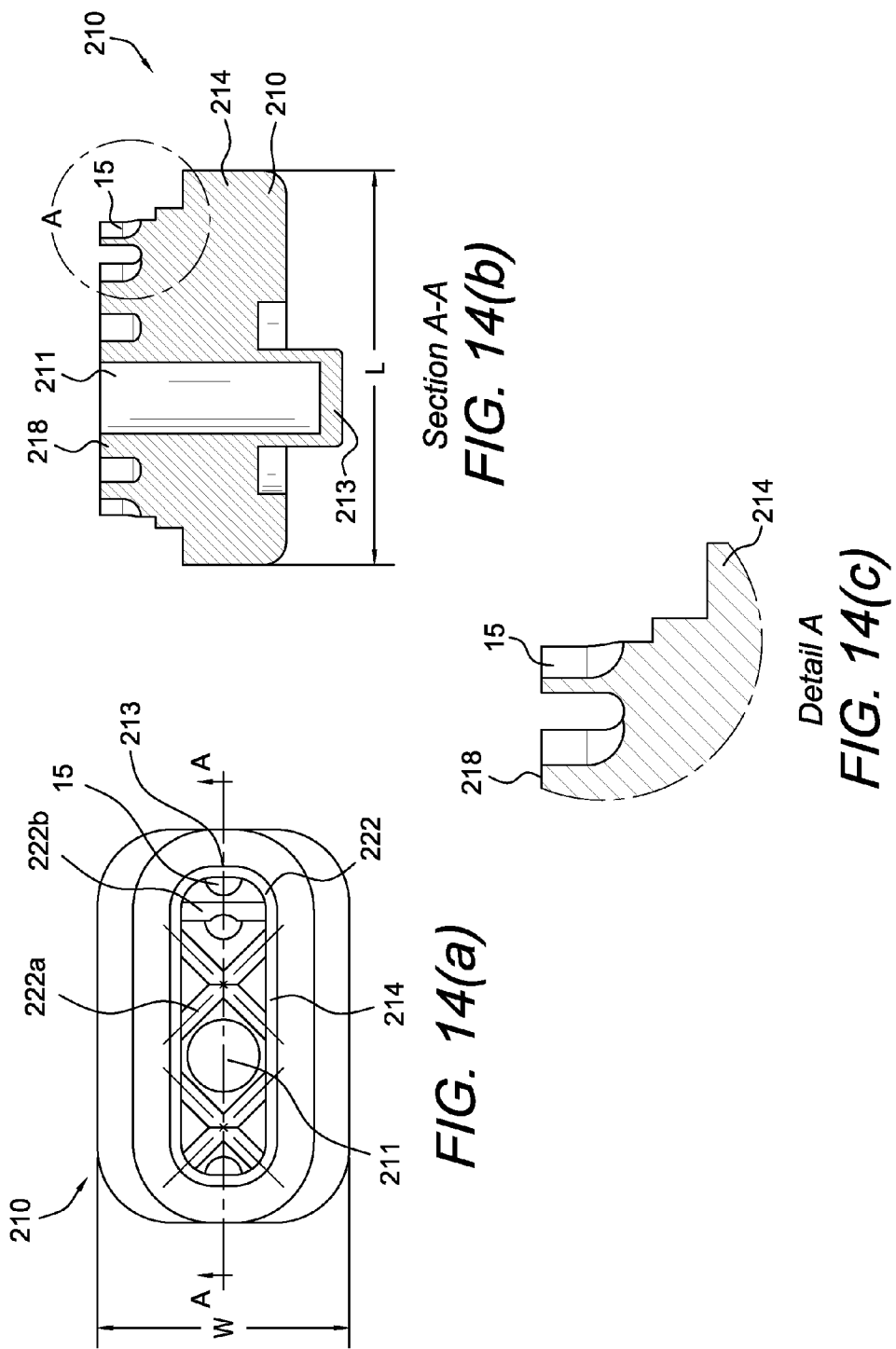

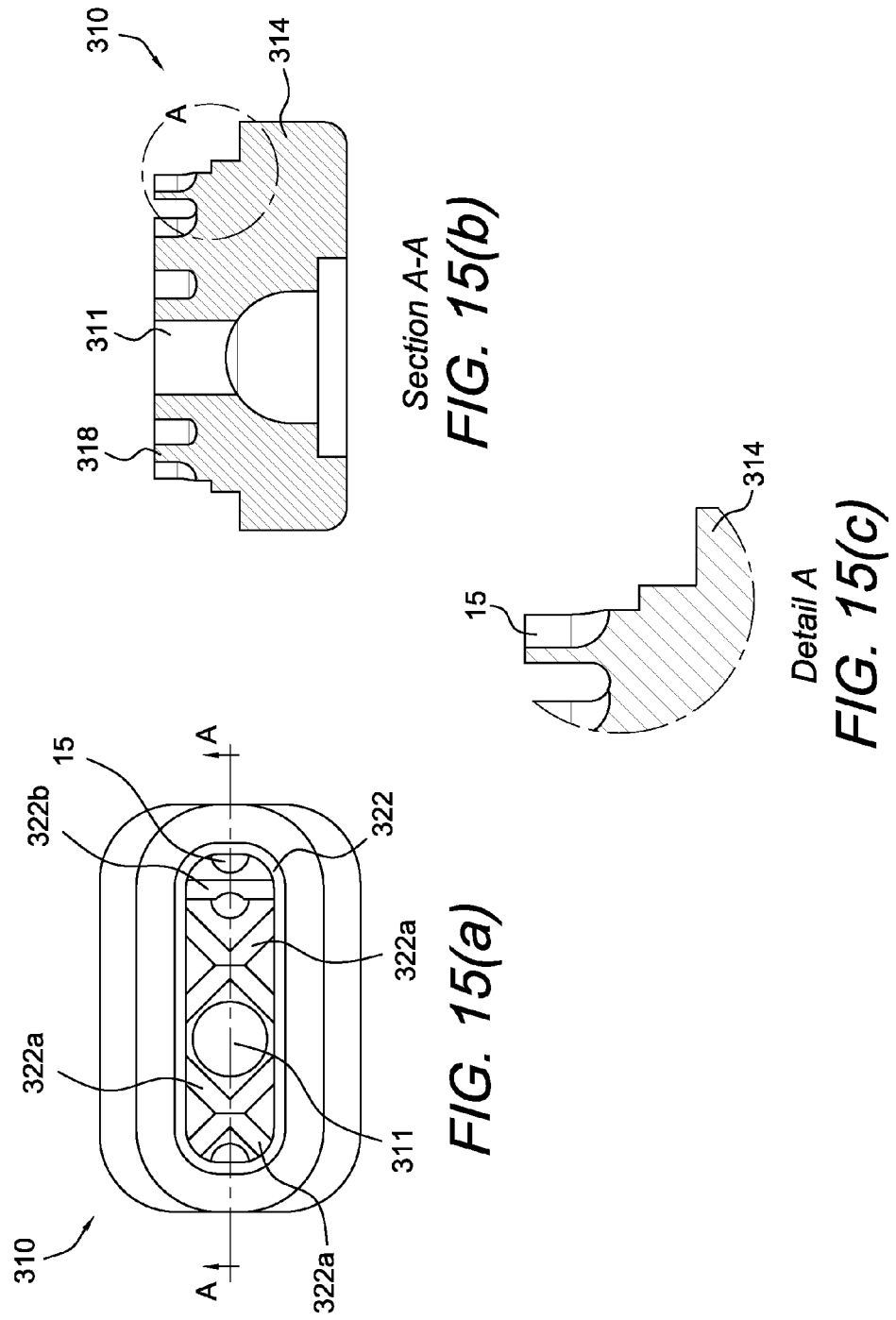

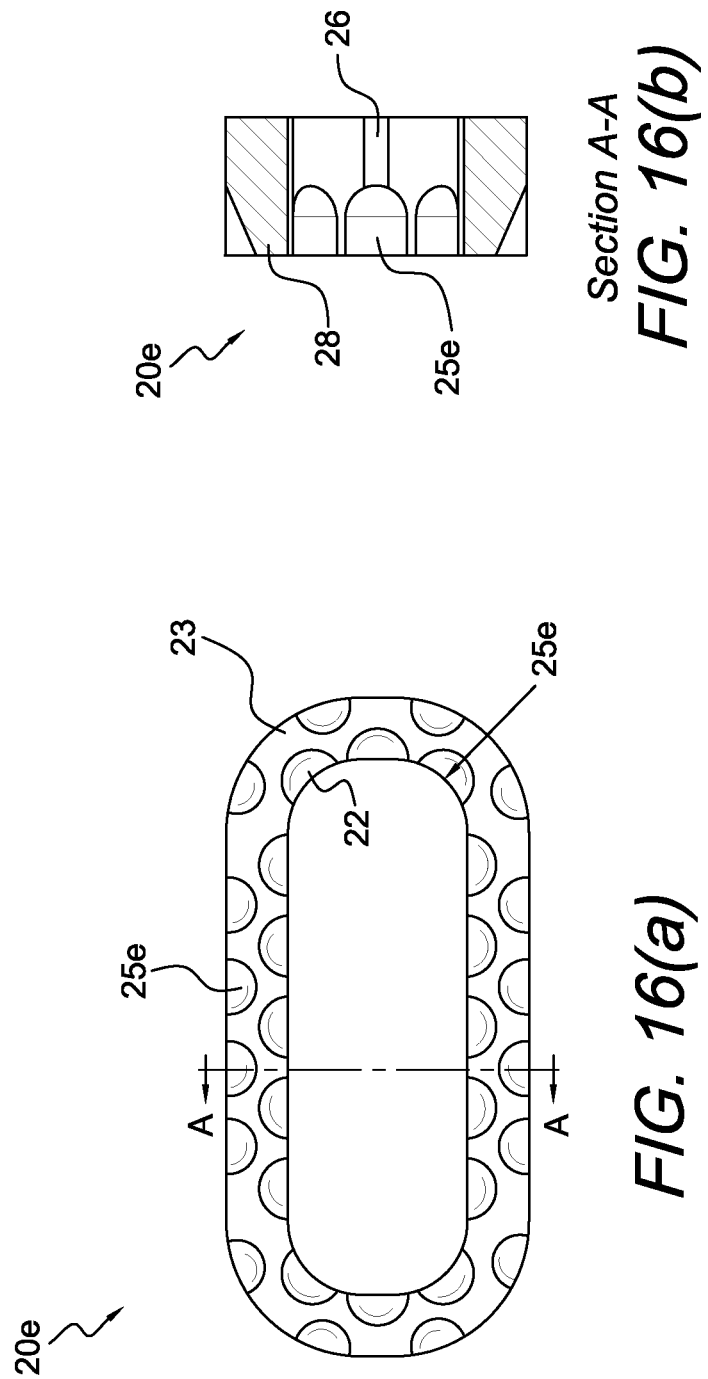

Section A-A

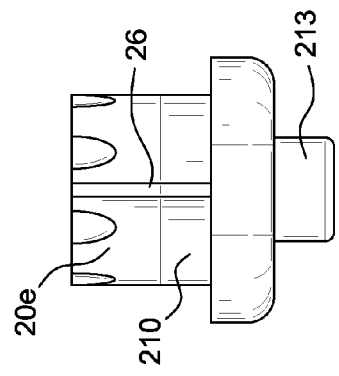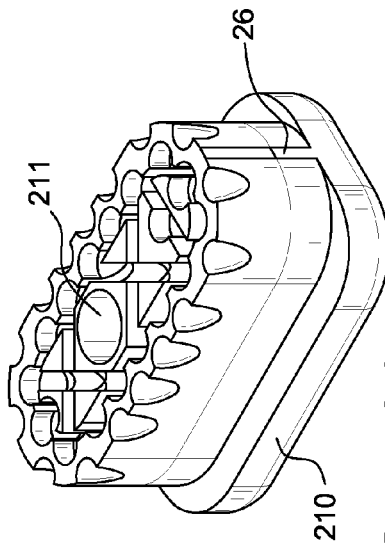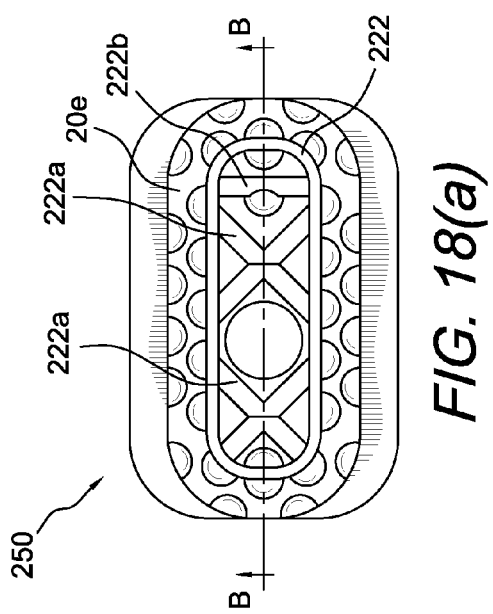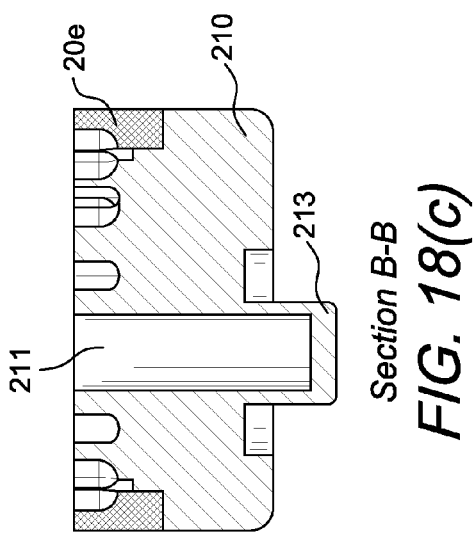

Detail A

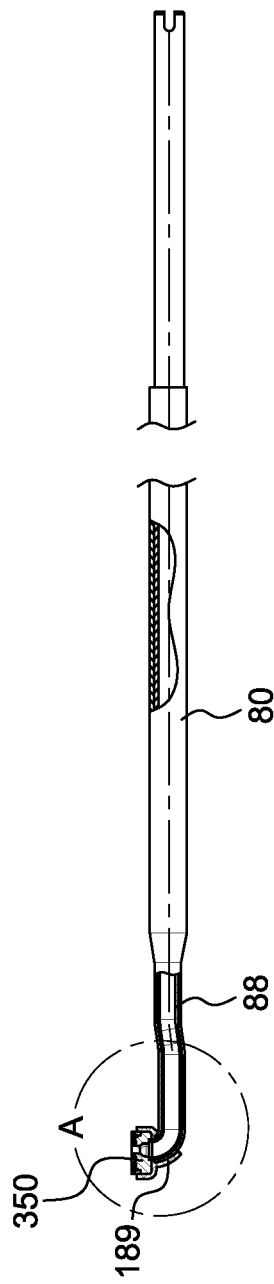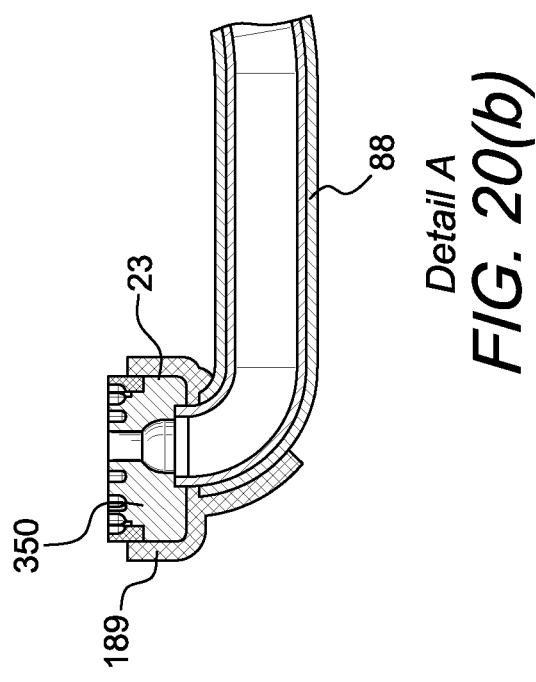

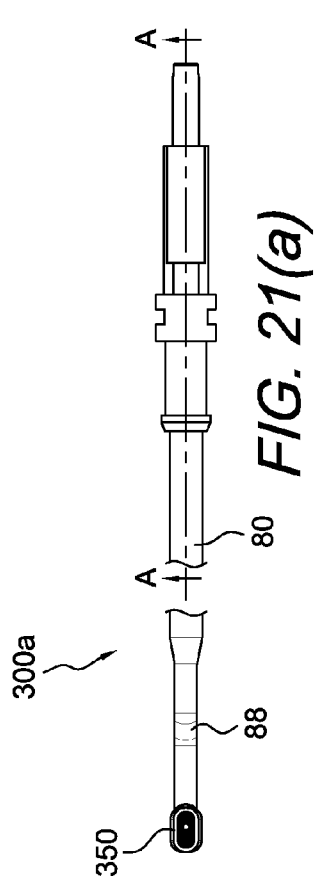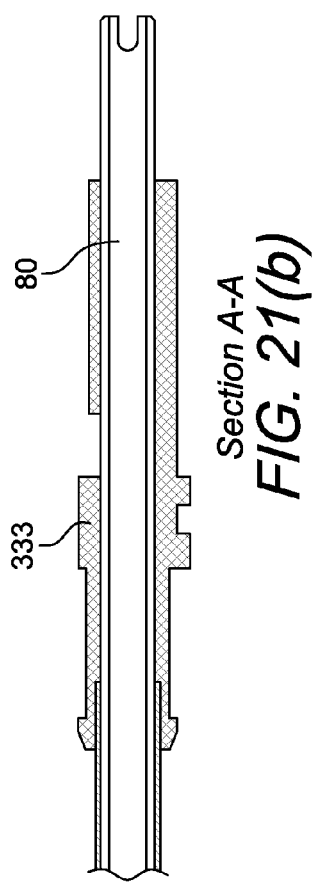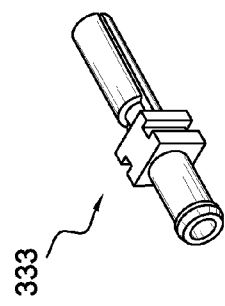

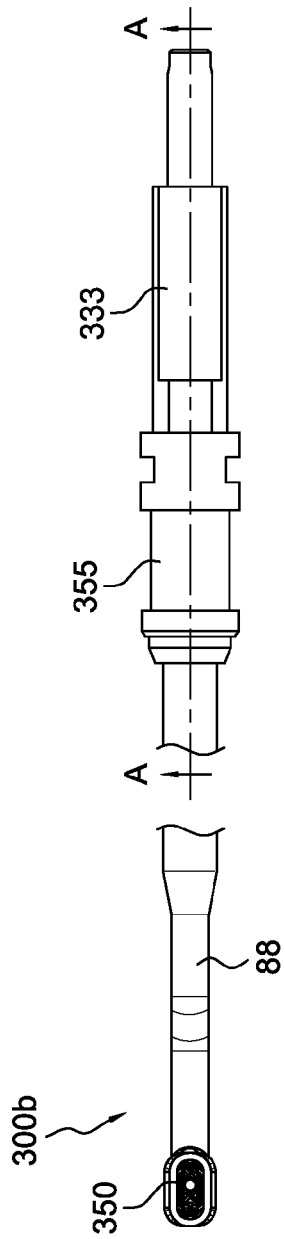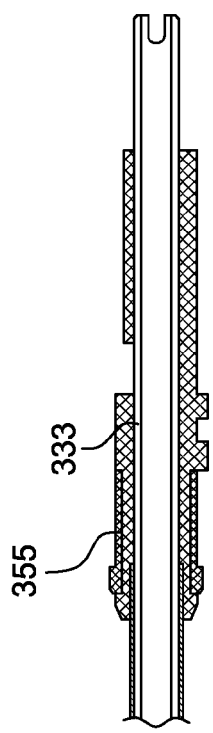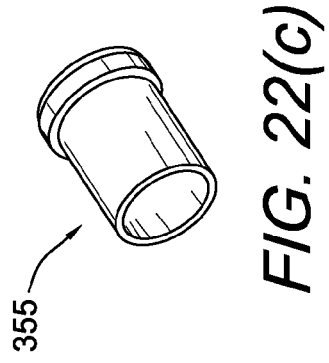
FIG. 22(a)
FIG. 22(b) Section A-A
FIG. 22(c)

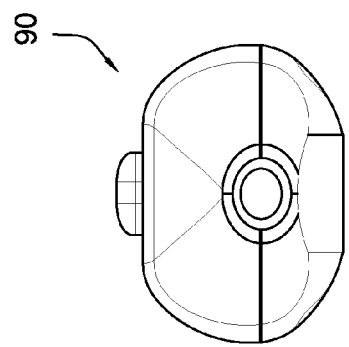
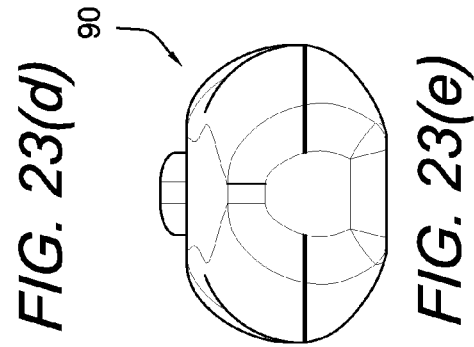
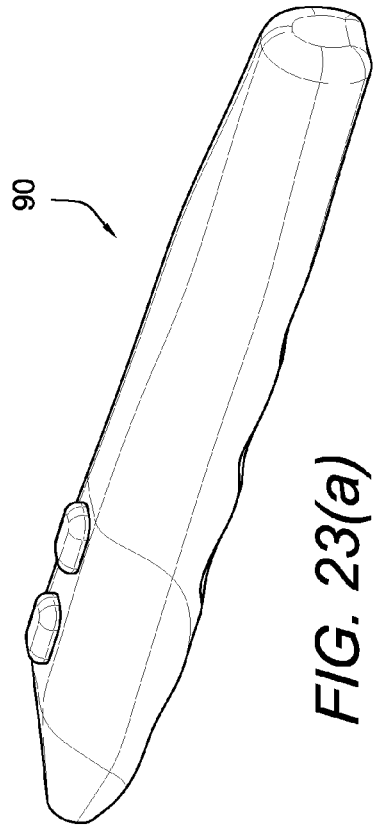
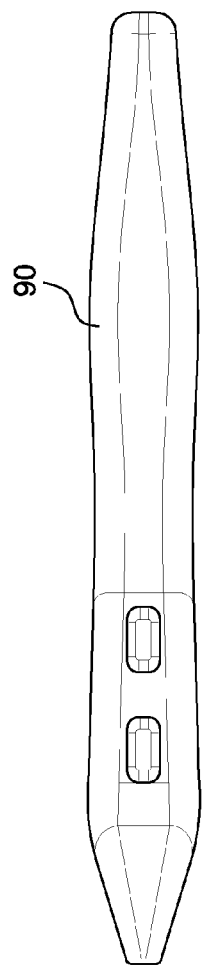

ABLATOR WITH SCALLOPED ELECTRODE AND SWAGED TUBE

CROSS-REFERENCE TO RELATED APPLICATIONS

This application claims the benefit of U.S. Provisional Application No. 61/138,039, filed Dec. 16, 2008, the entire disclosure of which is incorporated by reference herein. This application is also related to U.S. Publication No. 2007/0149965, the disclosure of which is incorporated by reference herein in its entirety.

FIELD OF THE INVENTION

The present application relates to the field of electrosurgery and, in particular, to electrosurgical devices and methods which employ high frequency voltage to cut, ablate or coagulate tissue in a fluid environment.

BACKGROUND OF THE INVENTION

Radiofrequency (RF) probes employed in electrosurgical procedures are generally divided into two categories: monopolar devices and bipolar devices. In monopolar electrosurgical devices, the RF current generally flows from an exposed active electrode through the patient's body, to a passive or return current electrode that is externally attached to a suitable location on the patient's skin. In bipolar electrosurgical device, both the active and the return current electrodes are exposed and are typically in close proximity. The RF current flows from the active electrode to the return electrode through the tissue. Thus, in contrast with the monopolar electrosurgical devices, the return current path for a bipolar device does not pass through the patient's body except for close proximity to the tip of the electrode.

Electrosurgery is the intentional passage of high frequency current through tissue to achieve a controlled surgical effect. This can be accomplished in an oxygen rich, an inert gas, or a conductive fluid media environment. Arthroscopic tissue ablation is performed in a conductive fluid environment, such as inside of a joint or body cavity filled with, for instance, normalized saline solution, and differs from that described previously in that current is conducted from the active electrode through the fluid to the return electrode. In the case of a monopolar device, the current flows through the patient to the return electrode in the manner previously described. In the case of bipolar devices operating in a conductive fluid environment, the return electrode is not in contact with tissue, but rather is submerged in the conductive fluid in the proximity of the active electrode. Current flow is from the active electrode through the conductive liquid and surrounding tissues to the return electrode of the bipolar device. Whether an electrode is monopolar or bipolar, current flows from all uninsulated surfaces of the active electrode to the return electrode anytime that the probe is energized. This is in contrast to conventional surgery (also called "open surgery") in which current flows only through electrode surfaces in contact with the patient's tissue.

During the past several years, specialized arthroscopic electrosurgical probes also called ablators have been developed for arthroscopic surgery. Ablators differ from the conventional arthroscopic electrosurgical probes in that they are designed for the bulk removal of tissue by vaporization, rather than by cutting the tissue or coagulating the bleeding vessels. This way, during ablation, volumes of tissue are vaporized rather then discretely cut out and removed from the surgical site. Aspiration ports in the ablator are often provided to remove ablated tissue and debris.

The power requirements of ablators are generally higher than those of other arthroscopic probes. The efficiency of the probe design and the characteristics of the radio frequency (RF) power supplied to the probe also affect the amount of power required for ablation. For example, probes with inefficient designs and/or powered by RF energy with poorly suited characteristics will require higher powers levels than those with efficient designs and appropriate generators. Probes used in electrosurgery have relatively large area of metallic electrode, which is the active area of the probe. Large electrode area decreases the probe impedance and, therefore, increases the RF power required for proper operation. The shape of the dielectric insulator and of the probe tip can significantly affect ablation. By properly shaping the insulator and the electrode tip, the threshold power can be substantially decreased.

A recent improvement to ablation electrodes is the addition of aspiration to remove bubbles and debris from the surgical site. During electrosurgery in a conductive fluid environment, tissue is vaporized, thereby producing steam bubbles which may obscure the view of the surgeon or displace saline from the area of the intra-articular space which the surgeon wishes to affect. In the case of ablation (bulk vaporization of tissue), the number and volume of bubbles produced is even greater than when using other electrodes since fluid is continually boiling at the active electrode during use. Ideally, flow through the joint carries these bubbles away; however, in certain procedures this flow is frequently insufficient to remove all of the bubbles. Aspiration removes some bubbles as they are formed by the ablation process, and others after they have collected in pockets within the joint. The aspiration portal is connected to an external vacuum source which provides suction for bubble evacuation.

Aspirating ablators are divided into two categories according to their level of flow. High-flow ablators have an aspiration tube, the axis of which is coaxial with the axis of the ablator rod or tube, which draws in bubbles and fluid through its distal opening and/or openings cut into the tube wall near its distal tip. High-flow ablators may decrease the average joint fluid temperature by removing heated saline (waste heat since it is an undesirable byproduct of the process) from the general area in which ablation is occurring. The effectiveness of the aspiration, both for removal of bubbles and for removal of waste heat, will be affected by the distance between the opening through which aspiration is accomplished and the active electrode. The distal tip of the aspiration tube is generally several millimeters distant proximally from the active electrode so as to not to obstruct the surgeon's view of the electrode during use. Decreasing this distance is desirable since doing so will increase the effectiveness of the aspiration. However, this must be accomplished without limiting the surgeon's view or decreasing the ablator's ability to access certain structures during use.

Low-flow ablators are those which aspirate bubbles and fluid through gaps in the ablating surfaces of the active electrode and convey them from the surgical site via means in the elongated distal portion of the device. Current low-flow ablators require increased power to operate as effectively as a nonaspirating or high-flow aspirating ablators because the low-flow aspiration draws hot saline from the active site of a thermal process. In the case of low-flow ablators, the heat removed is necessary process heat rather than the waste heat removed by high-flow ablators. Because of this, aspirating ablators of the low-flow type generally require higher power levels to operate than other ablators thereby generating more waste heat and increasing undesirable heating of the fluid within the joint.

Each of these types of aspirating ablation electrodes has its drawbacks. In the case of high-flow aspirating ablators, the aspiration tube increases the diameter of the device thereby necessitating the use of larger cannulae which, in turn, results in an increase in wound size and often an increase in patient pain and recovery time. In the case of low-flow aspirating ablators, the devices decrease the efficiency of the probes since process heat is removed from a thermal process. This decreased efficiency results in decreased rates of tissue removal for a given power level. This results in increased procedure times or necessitates the use of higher power levels to achieve satisfactory tissue removal rates. High power levels are undesirable as they cause increased heating of the fluid at the site and thereby increase the likelihood of thermal injury to the patient.

Accordingly, it is desirable to provide an electrosurgical probe of high efficiency and high impedance with an improved design of the aspiration port, and which is capable of conferring high ablation rates at low RF power levels. An electrosurgical ablation electrode with an advanced electrode and tube design is also desirable.

SUMMARY OF THE INVENTION

The present invention provides a surgical ablating instrument having an advanced electrode and tube design, with a swaged and bent one-piece metal tube that fits in small cannulas (as small as a 5.5 mm cannula). The electrode has a scalloped configuration that provides decreased surface area with more edges. The handle is provided with an ergonomic design that utilizes a bend with a cut at the end of the tube (for example, a 30 degree bend with a 15 degree cut). The surgical instrument may be provided with a novel insulative design.

Other features and advantages of the present invention will become apparent from the following description of the invention which refers to the accompanying drawings.

BRIEF DESCRIPTION OF THE DRAWINGS

FIG. 1(a) illustrates a perspective view of a scalloped electrode (with a 7-face scallop electrode base and a 10-face scallop electrode ring) according to an embodiment of the present invention.

FIG. 1(b) illustrates a perspective view of an scalloped electrode (with a 7-face scallop electrode base and a 20-face scallop electrode ring) according to an embodiment of the present invention.

FIGS. 2(a)-(d) illustrate a top view, perspective view, side view and cross-sectional view, respectively, of a 7-face electrode base (special machined configuration, and also illustrated in FIGS. 1(a) and 1(b)) of a scalloped electrode according to another embodiment of the present invention.

FIG. 6(a)-(c) illustrate a top view, cross-sectional view and perspective view, respectively, of a 10-face scallop electrode ring (special machined configuration) of a scalloped electrode according to another embodiment of the present invention.

FIGS. 7(a)-(c) illustrate a top view, side view and cross-sectional view, respectively, of a scalloped electrode (with a 7-face scallop electrode base and 20-face scallop electrode ring (metal assembly)) according to another embodiment of the present invention.

FIG. 8(a) illustrates a perspective view of an electrode assembly of the present invention, with a 30 degree swaged tube and with the scalloped electrode of FIGS. 1-7.

FIG. 8(b) illustrates an enlarged view of the distal end of the electrode assembly of FIG. 8(a).

FIG. 8(c) illustrates a side view of the electrode assembly of FIG. 8(a).

FIG. 8(d) illustrates an enlarged view of the distal end of the electrode assembly of FIG. 8(b).

FIG. 8(e) illustrates a view of the swaged area of the distal end of the electrode assembly of FIG. 8(d), taken along line A of FIG. 8(d).

FIG. 9(a) illustrates a perspective view of another electrode assembly of the present invention, with a compound 45 degree assembly (with a 30 degree swaged tube and with an insulated probe assembly (with a scalloped electrode)).

FIG. 9(b) illustrates a side view of the electrode assembly of FIG. 9(a).

FIG. 9(c) illustrates an enlarged view of the distal end of the electrode assembly of FIG. 9(b).

FIG. 10(a) illustrates a perspective view of another electrode assembly of the present invention, with a compound 90 degree assembly (with a 30 degree swaged tube and with an insulated probe assembly (with a scalloped electrode)).

FIG. 10(b) illustrates a side view of the electrode assembly of FIG. 10(a).

FIG. 10(c) illustrates an enlarged view of the distal end of the electrode assembly of FIG. 10(b).

FIG. 11(a) illustrates a side view of a distal end of a scalloped electrode assembly with a 45 degree swaged tube version, with a 30 degree bent and a 15 degree cut at the end of the tube, according to another embodiment of the present invention.

FIG. 11(b) illustrates a top view of a distal end of the scalloped electrode assembly of FIG. 11(a).

FIG. 12(a) illustrates a perspective view of a 7-face electrode plugged base (non-aspirating base) of a scalloped electrode according to another embodiment of the present invention.

FIG. 12(b) illustrates another perspective view of the 7-face electrode plugged base of FIG. 12(a).

FIGS. 12(c)-(e) illustrate a top view, a side view, and a cross-sectional view, respectively, of the 7-face electrode plugged base of FIG. 12(a).

FIGS. 14(a)-(c) illustrate a top view, a cross-sectional view, and a detailed view, respectively, of an exemplary electrode plugged base (special machined configuration, with a novel scallop and slot design, and a substantially rectangular configuration) of a scalloped electrode according to another embodiment of the present invention.

FIGS. 15(a)-(c) illustrate a top view, a cross-sectional view, and a detailed view, respectively, of an exemplary electrode aspirating base (special machined configuration, with a novel scallop and slot design, and a substantially rectangular configuration) of a scalloped electrode according to another embodiment of the present invention.

FIGS. 16(a) and (b) illustrate a top view and a cross-sectional view, respectively, of an exemplary 32-face scallop electrode ring (special machined configuration, and with a substantially rectangular configuration) of a scalloped electrode according to another embodiment of the present invention.

FIGS. 18(a)-(d) illustrate a top view, side view, cross-sectional view, and perspective view, respectively, of a non-aspirating scalloped electrode (with the exemplary electrode plugged base of FIGS. 14(a)-(c) and the exemplary 32-face scallop electrode ring of FIGS. 16(a) and (b)) according to another embodiment of the present invention.

FIG. 20(a) illustrates a side view of another electrode assembly of the present invention, with a compound 90 degree assembly (with a 30 degree swaged tube and with an insulated probe assembly (with the scalloped electrode of FIGS. 17(a)-(d)).

FIG. 20(b) illustrates an enlarged view of the distal end of the electrode assembly of FIG. 20(a).

FIG. 21(a) illustrates a top view of another electrode assembly of the present invention, with a 30 degree swaged tube, a scalloped electrode, and a first insulative overmold.

FIG. 21(b) illustrates a cross-sectional view of the assembly of FIG. 21(a).

FIG. 21(c) illustrates a perspective view of the first insulative overmold of the assembly of FIG. 21(a).

FIG. 22(a) illustrates a top view of the electrode assembly of FIG. 21(a) (having a 30 degree swaged tube, a scalloped electrode, and a first insulative overmold) and with an additional second insulative overmold.

FIG. 22(b) illustrates a cross-sectional view of the assembly of FIG. 22(a).

FIG. 22(c) illustrates a perspective view of the second insulative overmold of the assembly of FIG. 22(a).

FIGS. 23(a)-(e) illustrate a perspective view, top view, side view, and two end views, respectively, of an ablating device with a scalloped electrode assembly of the present invention.

DETAILED DESCRIPTION OF THE INVENTION

Figure 3C:
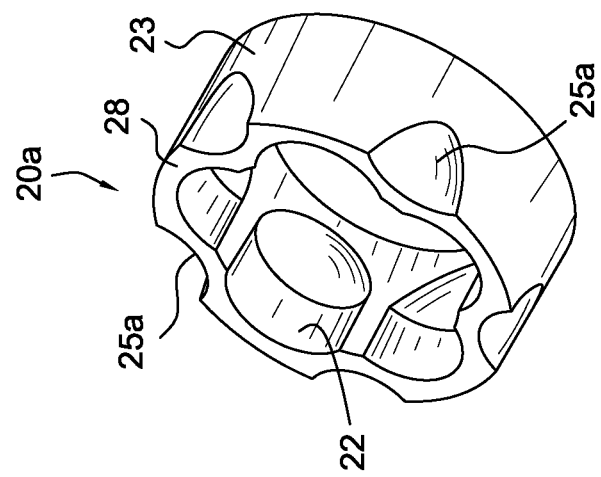
FIGS. 3(a)-(c) illustrate a top view, cross-sectional view and perspective view, respectively, of a 10-face scallop electrode ring (special machined configuration, and also illustrated in FIG. 1(a)) of a scalloped electrode according to another embodiment of the present invention.
Figure 3B:
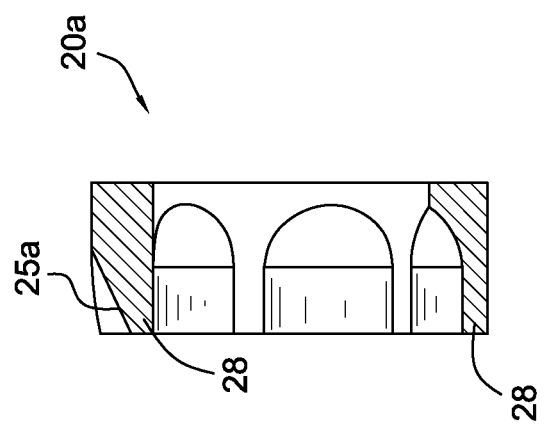
Figure 3A:
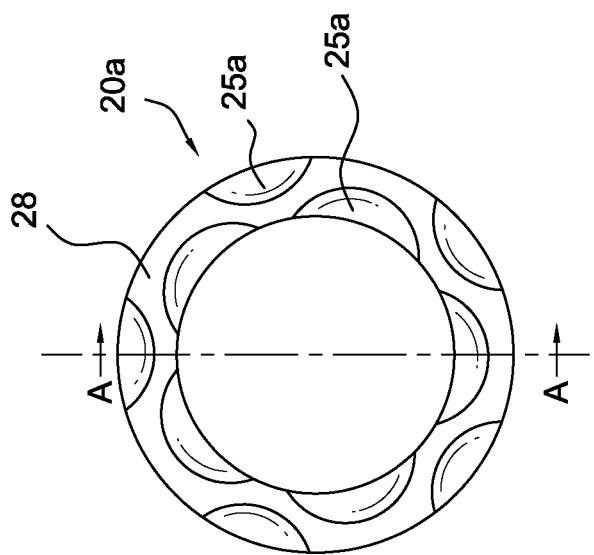

The present invention provides a surgical ablating instrument having an advanced electrode design, with a swaged one-piece metal tube that fits in a small cannula (as small as a 5.5 mm cannula, for example). The electrode has a scalloped configuration that provides decreased surface area with more edges (facets). The electrode may have an aspirating (i.e., suction through the electrode face) or a non-aspirating (or plugged or obstructed base) profile. The instrument may be provided with an advanced insulative overmold design.

The scallop electrode device of the present invention has a multi-facet design, delivers a maximum height offset between the electrode face and the coated shaft (for example, a 0.094 height offset with heat shrink), fits a small cannula (as small as a 5.5 mm diameter cannula, for example), provides suction through the electrode face, provides self-clearing suction pathway capabilities, does not require the use of a ceramic insulator, is heat-shrink compatible, is portable to various surgical application, reduces the suggested ESU power setting requirements, utilizes a more ergonomically-designed next generation handle, may incorporate a suction flow regulator scheme if required by a specific application (such as, for example, a suction flow regulator as described in U.S. Provisional Appl. No. 61/138,034, filed on Dec. 16, 2008), is gamma sterilizable, leverages MIM technology and is compatible with next generation packaging scheme.

Referring now to the drawings, where like elements are designated by like reference numerals, FIGS. 1-25 illustrate various structural elements of scalloped electrodes and assemblies of the present invention.

FIGS. 1-7 illustrate scalloped electrodes (with a scalloped base and a scalloped ring) according to embodiments of the present invention. The electrodes of FIGS. 1-7 are exemplary aspirating electrodes (i.e., aspiration and suction is conducted through the electrode). FIG. 8-11 illustrate various embodiments of swaged tubes that are employed with the electrodes of FIGS. 1-7. The probe assemblies of FIGS. 8-11 are exemplary 45 or 90 degree compound assemblies (with a 30 degree bend and a 15 degree cut at the end of the tube) that may be insulated or non-insulated.

Figure 13C:
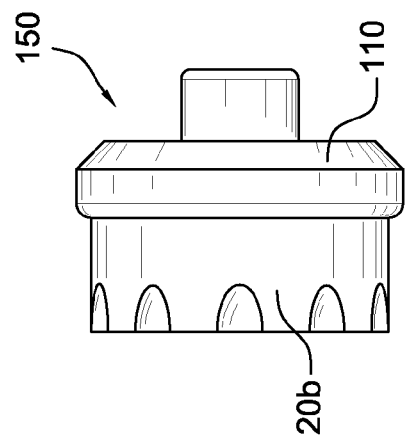
FIGS. 13(a)-(c) illustrate a top view, a cross-sectional view, and a side view, respectively, of a scalloped electrode (with a 7-face scallop electrode plugged base and with a 20-face scallop electrode ring (metal assembly)) according to another embodiment of the present invention.
Figure 13B:
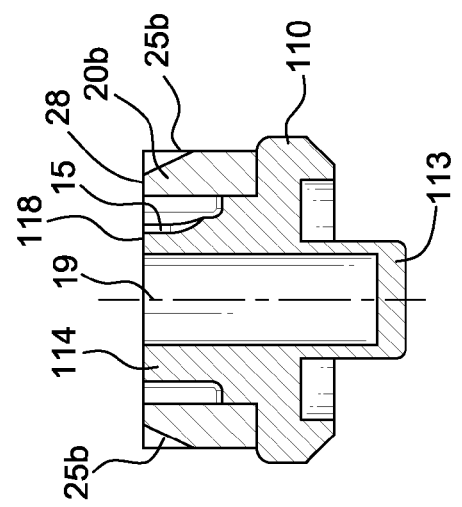
Figure 13A:
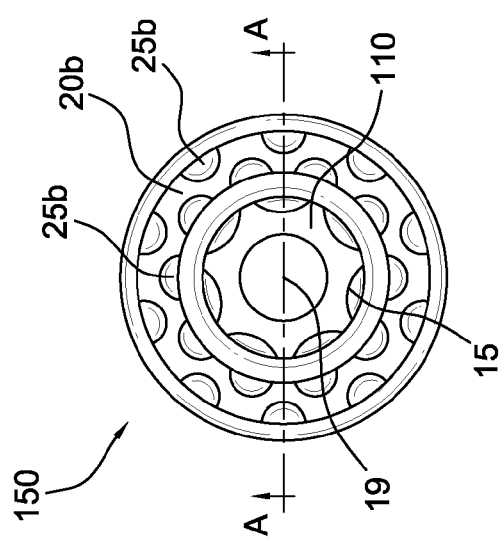
Figure 17B:
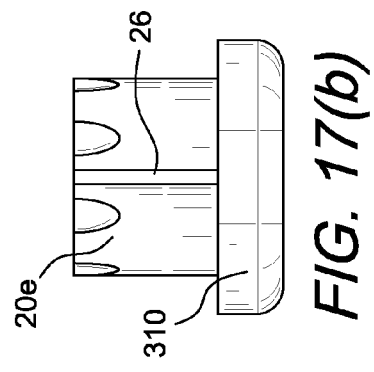
FIGS. 17(a)-(d) illustrate a top view, side view, cross-sectional view, and perspective view, respectively, of an aspirating scalloped electrode (with the exemplary electrode aspirating base of FIGS. 15(a)-(c) and the exemplary 32-face scallop electrode ring of FIGS. 16(a) and (b)) according to another embodiment of the present invention.
Figure 17D:
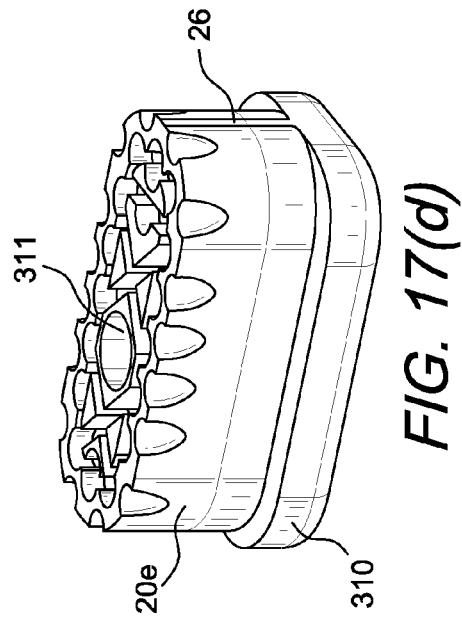
Figure 17A:
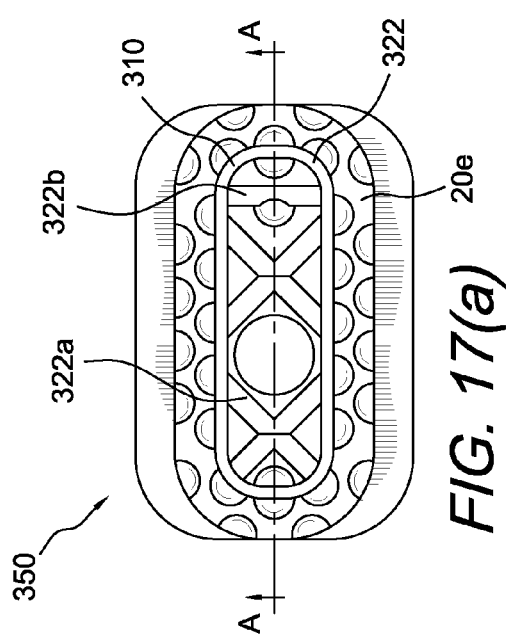
Figure 17C:
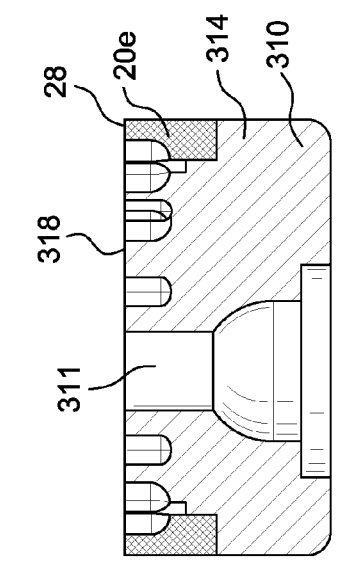

FIG. 12 illustrates views of a scalloped electrode base that has a non-aspirating or plugged design (i.e., aspiration and suction is not permitted through the electrode face). FIG. 13 illustrates an exemplary scalloped electrode (with the scalloped plugged base of FIG. 12 and a scalloped ring).

FIGS. 14-20 illustrates views of a scalloped electrodes and probe assemblies (with aspirating or non-aspirating designs) provided with electrode bases and rings having a combined scallop and slot design, and with a substantially rectangular cross-sectional views. These exemplary probe assemblies may be 45 or 90 degree compound assemblies (with a 30 degree bend and a 15 degree cut at the end of the tube) that may be insulated or non-insulated. FIGS. 21 and 22 illustrate details of a novel insulative design assembly of the present invention (with first and second overmolds).

The scalloped electrodes illustrated in the drawings have a scallop or scalloped design when viewed from a top view of the electrode, i.e., when viewed in a direction about perpendicular to a most distal surface of the electrode. As detailed below, these electrodes (base and/or ring) may have various cross-sectional shapes and geometries, for example, round or circular, elliptical, oval, square, or rectangular, or any combination of these geometries.

The scalloped electrodes include different numbers of edges or facets (grooves) machined within the electrode base and/or the electrode ring. These scalloped grooves may have a regular or irregular configuration, depending on the specific application. The scalloped grooves may be provided on either the inner surface or the outer surface, or both the inner and outer surfaces, of the electrode base or the electrode ring (or both the electrode base and the electrode ring). In certain embodiments, the electrode base may not be provided with a scalloped pattern, but only the ring electrode (with scalloped grooves provided on either the inner surface or the outer surface, or both the inner and outer surfaces, of the electrode ring). In other embodiments, the electrode ring may not be provided with a scalloped pattern, but only the base electrode (with scalloped grooves provided on either the inner surface or the outer surface, or both the inner and outer surfaces, of the electrode base). In yet other embodiments, the scalloped grooves are provided on both the base electrode and the ring electrode (with scalloped grooves provided on either the inner surface or the outer surface, or both the inner and outer surfaces, of each of the electrode base and electrode ring). The scalloped grooves may have a semi-circular or semi-elliptical shape and may be evenly spaced around an inner and/or outer surface of the base electrode or the ring electrode. The radii of the scalloped grooves may be similar or different. The radii of the scalloped grooves of the electrode base may be similar to or different from the radii of the scalloped grooves of the electrode ring.

For example, FIG. 1(a) illustrates a perspective view of an exemplary embodiment of a scalloped electrode 50a of the present invention, with a 7-face scallop electrode base and a 10-face scallop electrode ring 20a. FIG. 1(b) illustrates a perspective view of another scalloped electrode 50b, with a 7-face scallop electrode base 10 and a 20-face scallop electrode ring 20b.

Electrode base 10 of the scalloped electrodes of the present invention is illustrated in more detail in FIGS. 2(a)-(d). Grooves 15 are provided on the outer surface 13 of the tubular element 14 of the base 10, as shown in FIGS. 2(b) and 2(d), for example. A central lumen 11 of the base 10 is defined by the inner surface of the tubular member 14 (i.e., the surface opposite the outer surface 13 defining the grooves). Central lumen 11 provides direct aspiration flow and suction. When viewed from a top view of the electrode base, i.e., when viewed from a direction about perpendicular to a most distal surface of the tubular member 14, most distal surface 18 has a scallop or scalloped configuration.

In an exemplary embodiment, grooves 15 are machined within the electrode base. Grooves 15 may have a semi-circular or semi-elliptical shape (or a combination of these shapes) and may be evenly spaced around the outer surface 13 of the base electrode. The radii of the scalloped grooves 15 may be similar or different. The radii of the scalloped grooves 15 of the electrode base 10 may be similar to or different from the radii of the scalloped grooves of the electrode ring (detailed below). Scalloped grooves 15 may be provided in any number on surface 13 of the electrode base 10 (although the exemplary embodiment in the drawings shows seven machined grooves that are equally spaced apart around the circumference of the base, the invention is not limited to this specific embodiment, and contemplates any number of scalloped grooves on the inner and/or outer surfaces of the electrode base).

The electrode base 10 (with machined scalloped grooves 15) is preferably formed of electrically conductive materials such as metals and metal alloys, for example, stainless steel and stainless steel alloys, platinum and platinum alloys, gold and gold alloys, nickel and nickel alloys, titanium and titanium alloys, and molybdenum and molybdenum alloys, or combinations of such metals and metal alloys, among others.

FIGS. 3-6 illustrate various views and structural configurations of electrode rings 20a, 20b, 20c, 20d according to exemplary embodiments of the present invention. Grooves 25a, 25b, 25c, 25d are machined within the outer or the inner surface of the ring 20a, 20b, 20c, 20d, or both on the inner and outer surfaces. For example, FIGS. 3(a)-(c) illustrate a 10-face scallop electrode ring 20a (special machined configuration, and also shown in FIG. 1(a)) with grooves 25a provided on both inner surface 22 and outer surface 23 of the ring electrode 20a. In the exemplary embodiment shown in FIGS. 3(a)-(c), five grooves 25a are machined within inner surface 22 (FIG. 3(c)) of ring 20a, and five grooves 25a are machined within outer surface 23 (FIG. 3(c)) of ring 20a. Grooves 25a may have a semi-circular or semi-elliptical shape (or other configurations) and are evenly spaced around inner surface 22 and outer surface 23 of the ring electrode. When viewed from a top view of the electrode ring, i.e., when viewed from a direction about perpendicular to a most distal surface of the ring 20a, most distal surface 28 has a scallop or scalloped configuration. The radii of the scalloped grooves 25a may be similar or different. The radii of the scalloped grooves 25a of the inner surface 22 may be similar to or different from the radii of the scalloped grooves 25a on the outer surface 23.

Figure 4C:
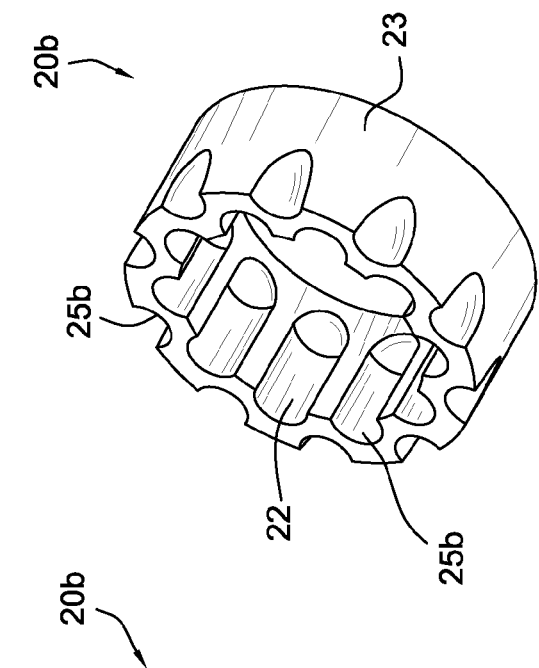
FIGS. 4(a)-(c) illustrate a top view, cross-sectional view and perspective view, respectively, of a 20-face scallop electrode ring (special machined configuration, and also illustrated in FIG. 1(a)) of a scalloped electrode according to another embodiment of the present invention.
Figure 4B:
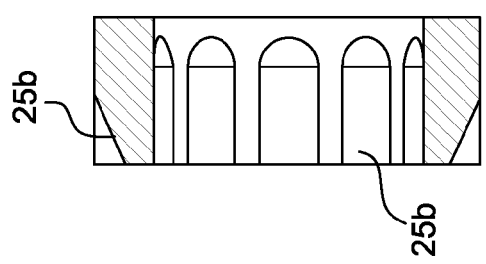
Figure 4A:
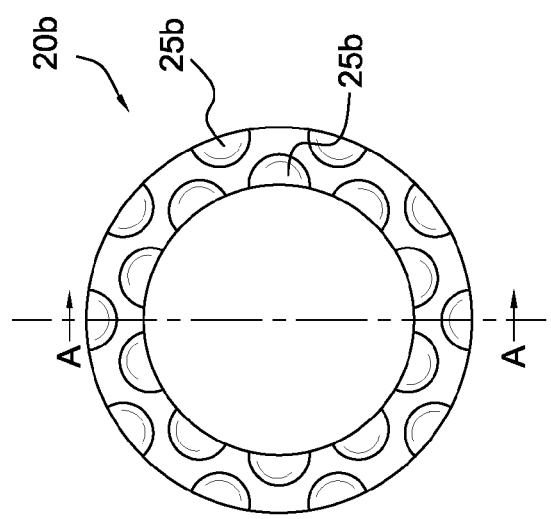

FIGS. 4(a)-(c) illustrate a 20-face scallop electrode ring 20b (special machined configuration, and also shown in FIG. 1(b)) of a scalloped electrode according to another embodiment of the present invention. Grooves 25b are provided on both inner surface 22 and outer surface 23 of the ring electrode 20b. In the exemplary embodiment of FIGS. 4(a)-(c), ten equally spaced, semi-circular or semi-elliptical structures or grooves 25b are provided within inner surface 22 (FIG. 4(c)) of ring 20b, and ten equally spaced, semi-circular or semi-elliptical structures or grooves 25b within outer surface 23 (FIG. 4(c)) of ring 20b. Grooves 25b are evenly spaced around inner surface 22 and outer surface 23 of the ring electrode 20b. The radii of the scalloped grooves 25b may be similar or different. The radii of the scalloped grooves 25b of the inner surface 22 may be similar to or different from the radii of the scalloped grooves 25b on the outer surface 23.

Figure 5C:
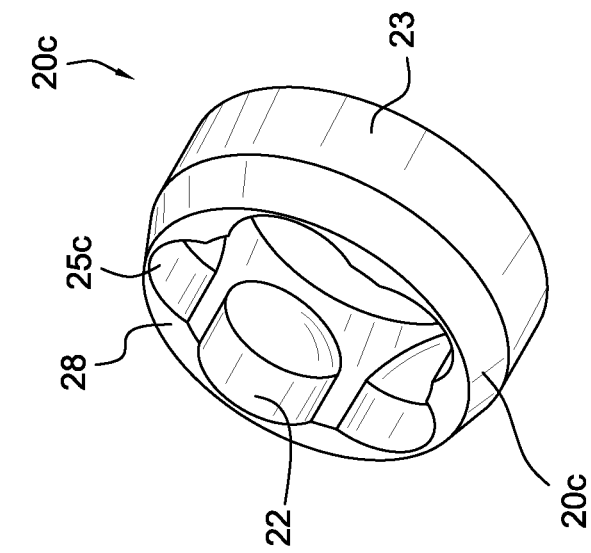
FIGS. 5(a)-(c) illustrate a top view, cross-sectional view and perspective view, respectively, of a 5-face scallop electrode ring (special machined configuration) of a scalloped electrode according to another embodiment of the present invention.
Figure 5B:
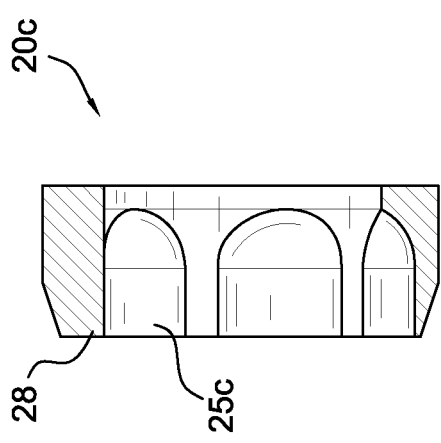
Figure 5A:
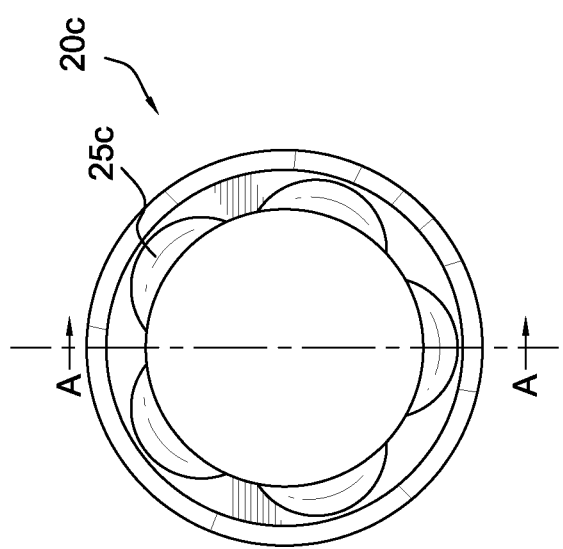

FIGS. 5(a)-(c) illustrate a 5-face scallop electrode ring 20c (special machined configuration) according to another embodiment of the present invention. Grooves 25c are provided only on inner surface 22 of the ring electrode 20c. These grooves are also semi-circular or semi-elliptical structures, and are evenly spaced around inner surface 22 of the ring electrode 20c. The radii of the scalloped grooves 25c may be similar or different.

FIG. 6(a)-(c) illustrate a scallop electrode ring 20d which is similar to that of FIGS. 5(a)-(c) but differs in that electrode ring 20d is provided with 10 grooves, i.e., it is a 10-face scallop electrode ring 20d (special machined configuration). Grooves 25d are provided only on the inner surface 22 of the ring electrode 20d. Grooves 25d are also semi-circular or semi-elliptical structures, and are evenly spaced around inner surface 22 of the ring electrode 20d. The radii of the scalloped grooves 25d may be similar or different.

Ring 20a, 20b, 20c, 20d (with scalloped grooves 25a, 25b, 25c, 25d) may be formed of a material similar to or different from that of the electrode base 10 (with machined grooves 15). Thus, ring 20a, 20b, 20c, 20d may be also formed of electrically conductive materials such as metals and metal alloys, for example, stainless steel and stainless steel alloys, platinum and platinum alloys, gold and gold alloys, nickel and nickel alloys, titanium and titanium alloys, and molybdenum and molybdenum alloys, or combinations of such metals and metal alloys, among others.

FIGS. 7(a)-(c) illustrate details of exemplary electrode 50b of the present invention (also shown in FIG. 1(b)), which is formed by assembling electrode base 10 of FIGS. 2(a)-(d) with the exemplary electrode ring 20b of FIGS. 4(a)-(c) (i.e., the 20-face scallop electrode ring 20*b*). Ring 20*b* is securely attached to base 10 by welding, for example, or by other known methods in the art. In the assembled state, tubular element 14 is concentric with the ring electrode 20*b*, and the most distal surface 18 of the tubular element 14 of the base 10 is about coplanar (coincides) with the most distal surface 28 of electrode ring 20*b* (as shown in FIG. 7(*c*), for example). Grooves 25*b* of the electrode ring 20*b* and grooves 15 of the base 10 form an alternating symmetrical pattern, as shown in FIG. 7(*a*). The grooves are evenly spaced relative to each of the tubular element 14 and the ring electrode 20*b*, and are also symmetrically located relative to a longitudinal axis 19 (FIGS. 7(*a*) and (*b*)) of the base 10 and ring 20*b*.

The electrodes of FIGS. 1-7 detailed above employ an electrode base 10 which has an aspirating profile (i.e., aspiration and suction is conducted through the central lumen 11 of the tubular member 14 of the base 10). FIG. 8-11 illustrate various embodiments of swaged tubes that are employed with the electrodes of FIGS. 1-7. The probe assemblies of FIGS. 8-11 are exemplary 45 or 90 degree compound assemblies (with a 30 degree bend and a 15 degree cut at the end of the tube) that may be insulated or non-insulated. For example, FIG. 8(*a*) illustrates a perspective view of an electrode assembly 100*a* of the present invention, with a one-piece 30 degree swaged and bent tube 80 and with a scalloped electrode (such as the exemplary scalloped electrode 50*b* of FIG. 1(*b*) or FIGS. 7(*a*)-(*c*)). As shown more clearly in FIG. 8(*d*), distal tube portion 88 of the tube 80 is swaged in that it forms an angle α of about 30 degrees with the tube 80 (i.e., longitudinal axis 81 of the tube 80 forms angle α with longitudinal axis 83 of the swaged portion 88). Longitudinal axis 19 of the electrode 50*b* forms an angle β (FIG. 8(*d*)) of about 45 degrees with the longitudinal axis 81 of the tube 80.

FIGS. 9(*a*)-(*c*) illustrate another electrode assembly 100*b* of the present invention, which is similar to the probe assembly 100*a* (in that probe assembly 100*b* is also a compound 45 degree assembly (with a 30 degree swaged tube)) but differs in that it is insulated. Insulator 89 is provided around the outer surface of the electrode face 23 of the electrode ring 20*b*, to surround the non-grooved area of the outer surface 23 of the electrode ring and to abut the machined grooves 25*b*.

Insulator 89 may comprise an insulating or dielectric material such as epoxy, plastic, silicon-based material, ceramic, glass or compositions of these mentioned materials, among many others. The dielectric material surrounds and insulates the metallic tip of the ablator electrode.

FIGS. 10(*a*)-(*c*) illustrates another electrode assembly 100*c* of the present invention, which is similar to the probe assembly 100*b* (in that probe assembly 100*c* has a 30 degree swaged tube and is insulated), but differs in that is a compound 90 degree assembly (and not a 45 degree assembly as in probe 100*b*). Longitudinal axis 19 of the electrode 50*b* forms an angle $β_1$ (FIG. 10(*c*)) of about 90 degrees with the longitudinal axis 81 of the tube 80.

FIGS. 11(*a*) and 11(*b*) illustrate additional views of the scalloped electrode assembly 100*a* of FIG. 8(*a*)-(*e*) with a 45 degree swaged tube version, with a 30 degree bent and a 15 degree cut at the end of the tube.

FIGS. 12(*a*)-(*e*) illustrate a scalloped electrode base 110 that has a non-aspirating or plugged design (i.e., aspiration and suction is not permitted through the electrode face), while FIGS. 13(*a*)-(*c*) illustrate an exemplary scalloped electrode (with the scalloped plugged base of FIG. 12(*a*) and a scalloped ring). Scalloped electrode base 110 is similar to the base 10 of FIGS. 2(*a*)-(*d*), in that grooves 15 are also provided on the outer surface 13 of tubular element 114 of the base 110 (in a manner and configuration similar to that of the grooves 15 of the base 10). However, lumen 111 of the base 110 (defined by the inner surface of the tubular member 114) is plugged by portion 113 so that no direct aspiration flow and suction is provided.

FIGS. 13(*a*)-(*c*) illustrate exemplary electrode 150 of the present invention, which is formed by assembling electrode non-aspirating base 110 of FIGS. 12(*a*)-(*e*) with the exemplary electrode ring 20*b* of FIGS. 4(*a*)-(*c*) (i.e., the exemplary 20-face scallop electrode ring 20*b*). Ring 20*b* is securely attached to base 110 by welding, for example, or by other known methods in the art. In the assembled state, tubular element 114 is concentric with the ring electrode 20*b*, and the most distal surface 118 of the tubular element 114 of the base 110 is about coplanar (coincides) with the most distal surface 28 of electrode ring 20*b* (as shown in FIG. 13(*b*), for example). Grooves 25*b* of the electrode ring 20*b* and grooves 15 of the base 110 form an alternating symmetrical pattern, as shown in FIG. 13(*a*). The grooves are evenly spaced relative to each of the tubular element 114 and the ring electrode 20*b*, and are also symmetrically located relative to a longitudinal axis 19 (FIGS. 13(*a*) and (*b*)) of the base 110 and ring 20*b*.

Reference is now made to FIGS. 14(*a*)-(*c*) which illustrate another exemplary embodiment of a scalloped electrode base 210 which is similar to the scalloped electrode base 110 of FIGS. 12(*a*)-(*e*) in that it has a non-aspirating or plugged design (i.e., aspiration and suction is not permitted through the electrode face), but differs from base 110 in that its cross-sectional view is a substantially rectangular view (and not circular, as for base 110), i.e., most distal surface 218 of non-aspirating base 210 has a scalloped rectangular configuration. The size of the scalloped electrode base 210 is also substantially bigger than that of electrode base 110 of FIGS. 12(*a*)-(*e*). In an exemplary embodiment, the length L (FIG. 14(*b*)) of the electrode base 210 is about 0.15 to about 0.2 inches, more preferably of about 0.172 inches, and the width W (FIG. 14(*a*)) of the electrode base 210 is about 0.1 to about 0.12 inches, more preferably of about 0.109 inches. Because of its increased size, the design of electrode base 210 also incorporates a plurality of slots or channels around the circumference of the base and also extending on the most distal surface 218 of the base. For example, FIG. 14(*a*) illustrates a wide slot 222 disposed all around the circumference of the electrode base, as well as slots 222*a* and 222*b* disposed in the exemplary-only pattern shown in FIG. 14(*a*) (i.e., with slots 222*a* forming a series of X patterns, and with slot 222*b* extending transversely between the two long edges or sides of the rectangular distal surface 218). Scalloped grooves 15 are also provided on the outer surface 213 of element 214 of the base 210 (in a manner and configuration similar to that of the grooves 15 of the base 110). Lumen 211 of the base 210 (defined by the inner surface of the tubular member 214) is plugged by portion 213 so that no direct aspiration flow and suction is provided.

FIGS. 15(*a*)-(*c*) illustrate another scalloped electrode base 310 which is similar to the base 210 of FIGS. 14(*a*)-(*c*) in that scalloped grooves 15 are provided adjacent slots 322*a* and 322*b* forming a series of X patterns, and extending transversely between the two long edges or sides of the rectangular distal surface 318, but differs from the base 210 in that base 310 has an aspirating or non-plugged design (i.e., aspiration and suction is permitted through the electrode face and lumen 311).

FIG. 16(*a*) and (*b*) illustrate an exemplary scallop electrode ring 20*e* having a substantially rectangular configuration (special machined configuration) that may be employed with the electrode bases 210, 310 described above (i.e., the inner width and inner length of the electrode ring 20*e* are about similar to the width and length of the electrode bases 210, 310). The exemplary electrode ring 20e of FIGS. 16(*a*) and (*b*) is a scalloped 32-face electrode ring with grooves 25e are provided on both inner surface 22 and outer surface 23 of the ring (with 16 grooves provided on each of the inner and outer surfaces). In the exemplary embodiment of FIGS. 16(*a*) and (*b*), five equally spaced, semi-circular or semi-elliptical structures or grooves 25e are provided on each of the two long lateral edges or sides of the inner surface 22 (FIG. 16(*a*)) of ring 20e, and four equally spaced, semi-circular or semi-elliptical structures or grooves 25e are provided on each of the two long lateral edges or sides of the outer surface 23 (FIG. 16(*a*)) of ring 20e. The remaining grooves 25e are spaced around the curved and short edges of both the inner and outer surfaces, as shown in FIG. 16(*a*). The radii of the scalloped grooves 25e may be similar or different. The radii of the scalloped grooves 25e of the inner surface 22 may be similar to or different from the radii of the scalloped grooves 25e on the outer surface 23. Electrode ring 20e is also provided with an additional transversal slot or channel 26 (as shown in FIG. 16(*b*)).

FIGS. 17(*a*)-(*d*) illustrate exemplary electrode 350 of the present invention, which is formed by assembling electrode aspirating base 310 of FIGS. 15(*a*)-(*c*) with the exemplary electrode ring 20e of FIGS. 16(*a*) and (*b*) (i.e., the exemplary 32-face scallop electrode ring 20e with a substantially rectangular configuration). Ring 20e is securely attached to base 310 by welding, for example, or by other known methods in the art. In the assembled state, the most distal surface 318 of the tubular element 314 of the base 310 is about coplanar (coincides) with the most distal surface 28 of electrode ring 20e (as shown in FIG. 17(*c*), for example). Grooves 25e of the electrode ring 20e, grooves 15 and slots 322, 322a, 322b of the base 310 form an alternating asymmetrical pattern, as shown in FIG. 17(*a*).

FIGS. 18(*a*)-(*d*) illustrate another exemplary electrode 250 of the present invention, which is similar to the electrode 350 detailed above in that it includes exemplary electrode ring 20e of FIGS. 16(*a*) and (*b*), but differs in that it includes the non-aspirating or plugged base 210 of FIGS. 45(*a*)-(*c*).

Figure 19A:
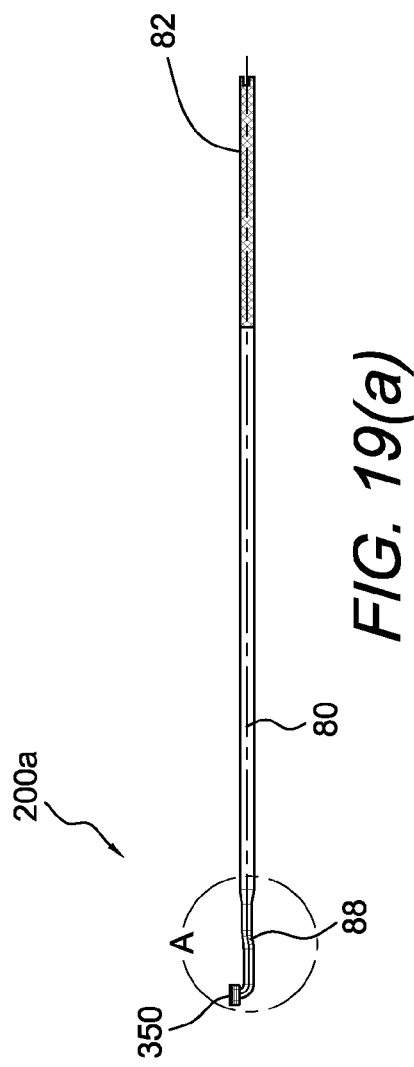
FIG. 19(a) illustrates a side view of another electrode assembly of the present invention, with a compound 90 degree assembly (with a 30 degree swaged tube and with the scalloped electrode of FIGS. 17(a)-(d)).
Figure 19B:
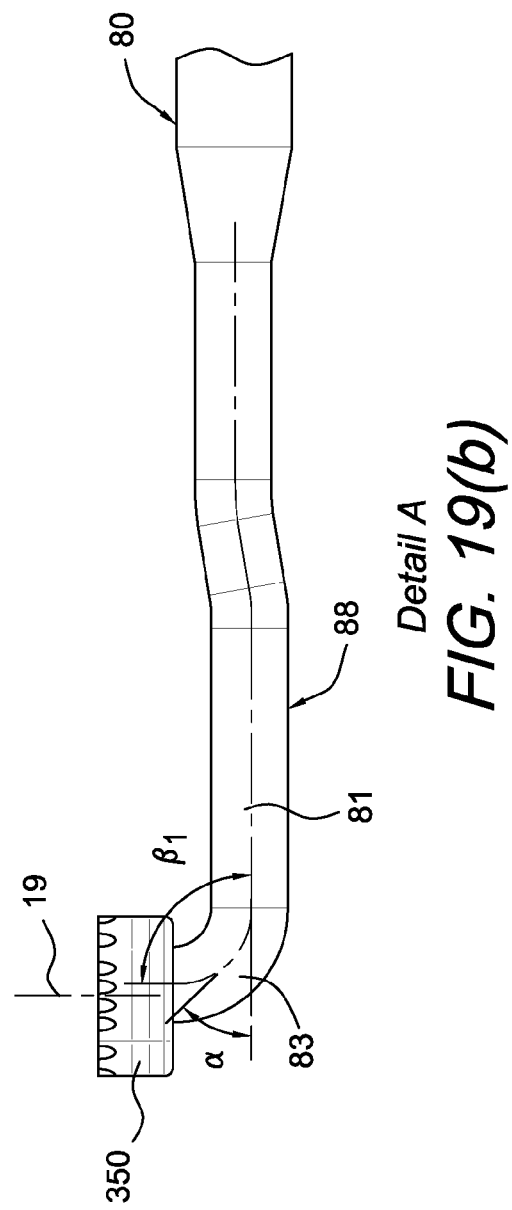
FIG. 19(b) illustrates an enlarged view of the distal end of the electrode assembly of FIG. 19(a).

FIGS. 19(*a*) and (*b*) illustrate an exemplary probe assembly 200a with one of the electrodes 250, 350 detailed above and with swaged tubes according to the present invention. The probe assembly of FIGS. 19(*a*) and (*b*) is an exemplary 90 degree compound assembly (with a 30 degree bend and a 15 degree cut at the end of the tube) that may be insulated or non-insulated. Electrode assembly 200a of the present invention is provided with a one-piece 30 degree swaged and bent tube 80 and with a scalloped electrode (such as the exemplary scalloped electrode 350). As shown more clearly in FIG. 19(*b*), distal tube portion 88 of the tube 80 is swaged in that it forms an angle α of about 30 degrees with the tube 80 (i.e., longitudinal axis 81 of the tube 80 forms angle α with longitudinal axis 83 of the swaged portion 88). Longitudinal axis 19 of the electrode 250 forms an angle $β_1$ (FIG. 19(*b*)) of about 90 degrees with the longitudinal axis 81 of the tube 80.

Figure 20E:
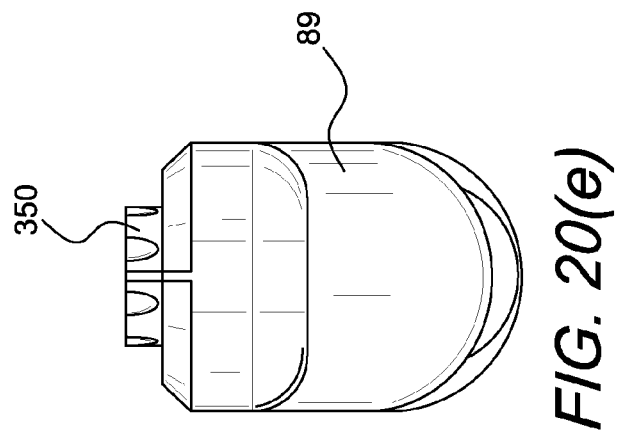
FIGS. 20(c)-(e) illustrate a top view, lateral view, and side view, respectively, of the assembly of FIG. 20(b).
Figure 20C:
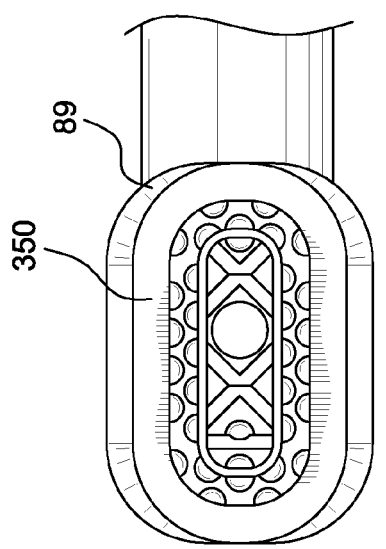
Figure 20D:
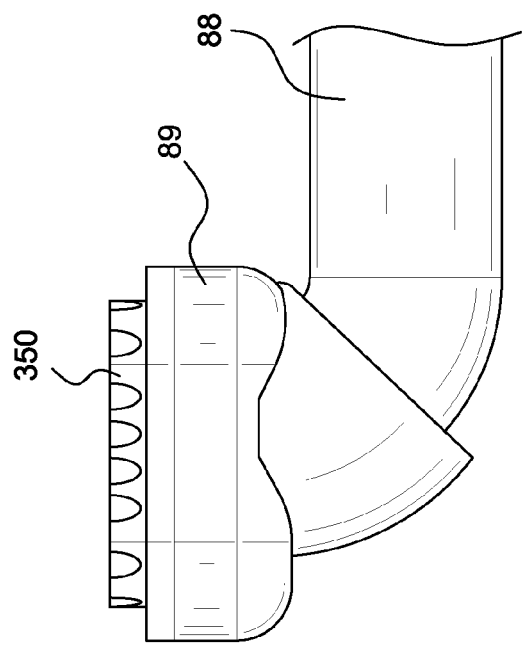

FIGS. 20(*a*)-(*e*) illustrate another electrode assembly 200b of the present invention, which is similar to the probe assembly 200a (in that probe assembly 200b is also a compound 90 degree assembly (with a 30 degree swaged tube) with a scalloped rectangular electrode) but differs in that it is insulated. Insulator 189 is in the form of a distal hood and is provided around the outer surface of the electrode face 23 of the electrode ring 20e, to surround the non-grooved area of the outer surface 23 of the electrode ring and to abut the machined grooves 25e.

Insulator 189 may comprise an insulating or dielectric material such as epoxy, plastic, silicon-based material, ceramic, glass or compositions of these mentioned materials, among many others. The dielectric material surrounds and insulates the metallic tip of the ablator electrode. Insulator 189 is provided as an overmold and surrounds at least part of PTFE Heat Shrink tube 88. Due to the contour of the electrode head, normal Heat Shrink does not provide an intimate insulative seal about the electrode body and, thus, the overmold configuration is necessary. The overmold configuration will be injection molded directly to the electrode and acts as a bridge to the Heat Shrink running proximally back into the handle.

FIGS. 21 and 22 illustrate details of a novel insulative design assembly of the present invention. FIGS. 21(*a*)-(*c*) illustrate electrode assembly 300a of the present invention, with a 30 degree swaged tube, a scalloped electrode (such as scalloped electrode 350 with or without an insulating hood 189 around it) and with a first insulative overmold 333. The first insulative overmold 333 is provided surrounding at least a portion of tube 80 and allows for proper nesting into the handle during production. Overmold 333 ensures precise orientation of the distal tip relative to the buttons on the upper case portion of the handle. This aspect provides repeatability in insulated probe placement from device to device. Overmold 333 is also a structural member providing resistance to both tensile and torsional loading by the user during clinical use.

FIGS. 22(*a*)-(*c*) illustrate another electrode assembly 300b of the present invention, with a 30 degree swaged tube, a scalloped electrode (such as scalloped electrode 350 with or without an insulating hood 189 around it), with the insulative overmold 333 of FIGS. 21(*a*)-(*c*), and also with a second insulative overmold 355. The second insulative overmold 355 is provided surrounding at least a portion of the first overmold 333 and of the tube 80. The second overmold 355 acts as a fluid seal, inhibiting fluid from entering the primary contact area where the metal contact from the integral PCB in the upper case of the handle makes intimate contact with the exposed proximal end of the probe assembly. In an exemplary embodiment, a plurality of ribs (for example, three small ribs) are provided in both the upper case and lower case portions of the handle to compress portions of the second overmold 355 and create a torturous path for any distal handle fluid ingress. The ultrasonic welding operation, which compresses and seals the perimeter of the case halves, provides the preload of the ribs against the second overmold 355.

FIGS. 23(*a*)-(*e*) illustrate various views of an ablating device with a scalloped electrode and an improved handle design (a "knuckle" electrode) of the present invention.

Figure 24:
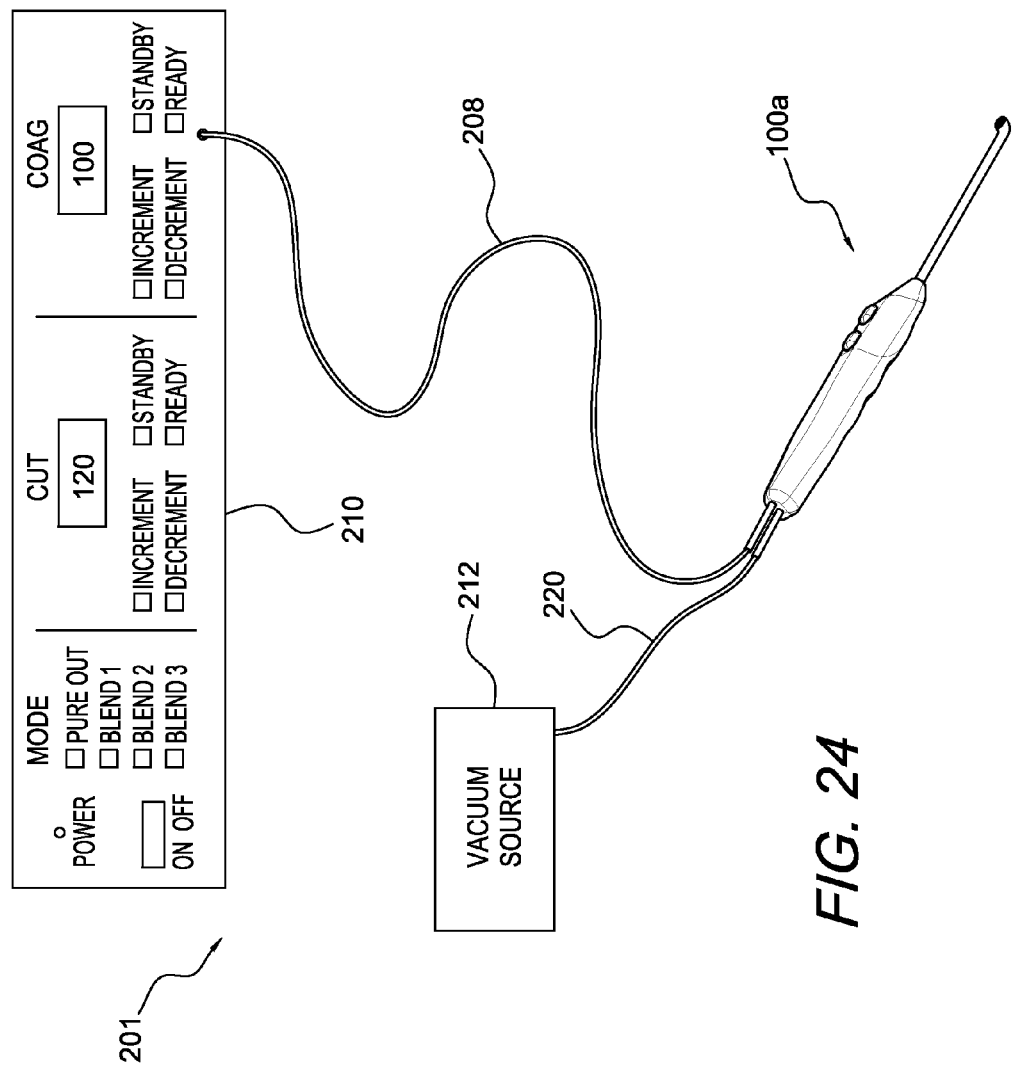
FIG. 24 is a schematic representation of an electrosurgical system according to the principles of the present invention.

FIG. 24 schematically illustrates an electrosurgery system 201 employing an electrosurgical scalloped probe (ablator) 100a, 100b, 100c, 200a, 200b, 300a, 300b of the present invention. Probe 100a, 100b, 100c, 200a, 200b, 300a, 300b is connected by electrical cable 208 to electrosurgical generator 210, and by tube 220 to an external vacuum source 212. A return electrode (not shown) is connected to the electrosurgical generator to provide a return path for the RF energy. The return electrode may be a dispersive pad attached to the patient at a site remote from the surgical site, or may be in proximity to the active electrode in contact with tissue or the conductive liquid.

The scalloped ablator 100a, 100b, 100c, 200a, 200b, 300a, 300b of the present invention may be used in a conventional open surgery environment or in other, less invasive, techniques that use cannulas or various port access devices if conductive fluid is present. The present invention has also applications in surgical procedures where the target tissue is flooded with, or submerged in, an electrically conductive fluid such as in many arthroscopic procedures for ablation, coagulation, shaping and cutting of various body parts such as the knee, shoulder, hip, ankle, elbow, hand or foot.

Surgical procedures using the scalloped ablator 100a, 100b, 100c, 200a, 200b, 300a, 300b of the invention include introducing the probe assembly in close proximity to the surgical site through an artificial conduit or a cannula, or through a natural conduit which may be in an anatomical body cavity or space or one created surgically. For the purposes of the present invention, the terms "close proximity" and "proximity" are defined as "in contact with" or "at a distance of about 0.1 to about 20 millimeters." The cavity or space may be distended during the procedure using a fluid or may be naturally held open by anatomical structures. In addition, the surgical site may be bathed in a continuous flow of conductive fluid, such as saline solution, to fill and distend the cavity. The procedures may include simultaneous viewing of the site via an endoscope or using an indirect visualization means.

Figure 25:
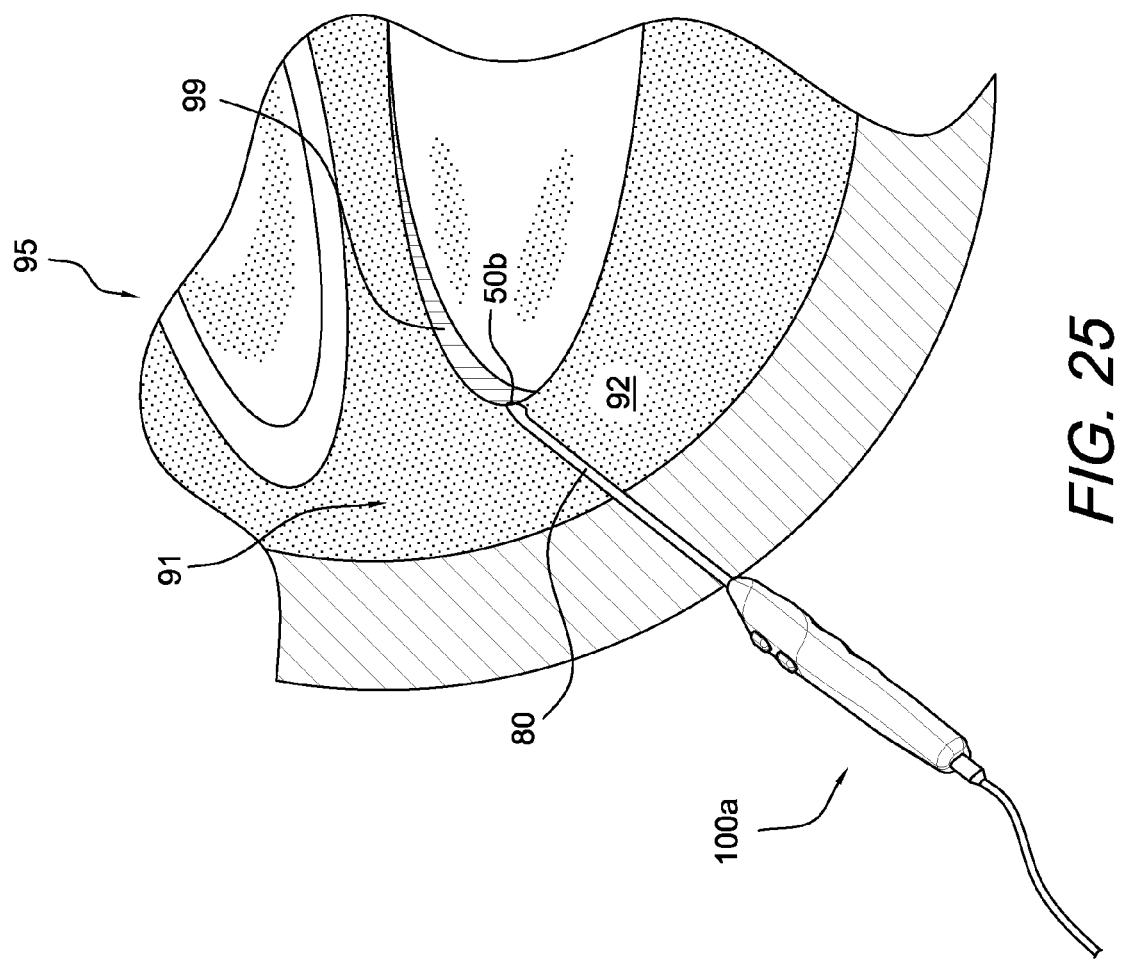
FIG. 25 is a schematic cross-sectional view of a knee joint undergoing an electrosurgical procedure employing a scalloped electrode assembly of the present invention.

FIG. 25 illustrates a schematic cross-sectional view of a knee joint region 95. The knee joint region 95 of FIG. 16 may undergo an arthroscopic procedure, for example, with electrosurgical ablator 100a, 100b, 100c, 200a, 200b, 300a, 300b fabricated according to the present invention. As known in the art, an endoscope (not shown) may be provided at one end with the distal tube 80 having the swaged design and the scalloped electrode 50b (for example), and then introduced into knee cavity 92 containing electrically conductive fluid 91 (FIG. 25) and in close proximity to target tissue 99 (FIG. 25). If the target tissue 99 of the knee joint region 95 is a damaged meniscus, for example, then target tissue 99 may undergo a partial or complete electrosurgical meniscectomy using active scalloped electrode of the present invention. Alternatively, the endoscope may be introduced separately from the electrosurgical electrode, via separate access means in a surgical technique commonly known as triangulation. In any event, knee cavity 92 may be distended during the arthroscopic procedure using electrically conductive fluid 91, so that target tissue 99 may be bathed in a continuous flow of conductive fluid 91, which may be preferably a saline solution.

Once the scalloped electrode 50b is positioned in the proximity of the target tissue 99 and the target tissue 99 is submerged in the electrically conductive fluid 91, the electrosurgical probe is energized by the electrosurgery power supply. The power supply delivers radio frequency energy, typically in the range of 100 kHz to 3 MHz, through a cable system to the electrosurgical electrode 100a and further to the distal active electrode 50b.

The improved design of the electrode, as well as of the swaged one-piece metal tube, confer the following advantages: hand control activation; for certain embodiments, aspiration through the electrode face; low power requirements; self clearing suction pathway; improved offset between the electrode face and the coated probe neck; ability to fit a 5.5 mm diameter cannula; and portability to other ESU consoles. The electrode of the ablator of the present invention does not require the use of a ceramic insulator, is heat shrink compatible, utilizes a more ergonomically designed handle, is gamma sterilizable, leverages MIM technology, and uses next generation packaging technologies.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed as new and desired to be protected by Letters Patent of the United States is:

1. An electrosurgical ablator comprising:
a shaft having a proximal end and a distal end, the shaft being a swaged and bent one-piece metal tube; and
at least one active electrode located at or near the distal end of the shaft including an electrode base provided with a tubular member defining a central lumen and an electrode ring attached to the electrode base, the electrode ring surrounding the electrode base, wherein a most distal surface of the electrode base and of the electrode ring has a scalloped configuration, and wherein the electrode base and the electrode ring are formed of an electrically conductive material.

2. The electrosurgical ablator of claim 1, wherein the central lumen is an aspiration lumen.

3. The electrosurgical ablator of claim 2, wherein the aspiration lumen is a tubular member comprising a wall having an outer surface and an inner surface.

4. The electrosurgical ablator of claim 1, wherein the central lumen is a non-aspirating central lumen.

5. The electrosurgical ablator of claim 1, wherein the tubular member comprises a wall having an outer surface and an inner surface, the outer surface being provided with a plurality of grooves that are equally spaced from each other.

6. The electrosurgical ablator of claim 5, wherein the plurality of grooves are provided in a scallop pattern or a partial scallop pattern.

7. The electrosurgical ablator of claim 6, wherein the plurality of grooves have a semi-circular or semi-elliptical configuration, or a combination of such configurations.

8. The electrosurgical ablator of claim 1, wherein the electrode base comprises a material which is similar to that of the electrode ring.

9. The electrosurgical ablator of claim 1, wherein the electrode base is integral with the electrode ring.

10. The electrosurgical ablator of claim 1, wherein the electrode base is provided as a separate component from the electrode ring.

11. The electrosurgical ablator of claim 1, wherein a longitudinal axis of the active electrode forms an angle of about 90 degrees or of about 45 degrees with a longitudinal axis of the shaft.

12. An electrosurgical ablator comprising:
a shaft having a proximal end and a distal end, the shaft being a swaged and bent one-piece metal tube; and
at least one active electrode located at or near the distal end of the shaft, wherein the at least one active electrode comprises an electrode base and a ring attached to the electrode base, wherein a most distal surface of at least one of the electrode base and the ring has a scalloped configuration, the electrode base comprising a tubular member with a wall having an outer surface and an inner surface, the outer surface being provided with a plurality of scalloped grooves that are equally spaced from each other, wherein the electrode base is provided with a central lumen which is non-aspirating when the electrosurgical ablator is in working mode, and wherein the electrode base and the electrode ring are formed of an electrically conductive material.

13. The electrosurgical ablator of claim 12, wherein the most distal surface of the active electrode is defined by the plurality of scalloped grooves and at least one channel adjacent the scalloped grooves.

14. The electrosurgical ablator of claim 12, wherein the active electrode is surrounded by an insulative material in the shape of a hood.

15. The electrosurgical ablator of claim 12, wherein the shaft is bent to allow insertion through a cannula with a diameter of about 5.5 mm.

16. The electrosurgical ablator of claim 12, wherein the shaft comprises at least a swaged portion and a straight portion, and at least one insulative overmold surrounding the straight portion.

17. An active electrode of an ablator, comprising:
an electrode base comprising a first tubular member having a first outer surface and a first inner surface, wherein the first outer surface has a regular polygonal shape when viewed in a cross-sectional view and wherein the first outer surface is provided with a first plurality of recesses so that the electrode base has a first scalloped configuration when viewed in a distal cross-sectional view;
an electrode ring attached to the electrode base and surrounding the electrode base, the electrode ring comprising a second tubular member disposed concentric with the first tubular member of the electrode base, the second tubular member having a second outer surface and a second inner surface, wherein at least one of the second inner and outer surfaces is provided with a second plurality of recesses so that the electrode ring has a second scalloped configuration, and wherein the electrode base and the electrode ring are formed of an electrically conductive material; and
an insulator provided on the second outer surface of the electrode ring.

18. The active electrode of claim 17, wherein the electrode base is a 7-face scalloped electrode base and the electrode ring is one of a 5-face, 10-face or 20-face scalloped electrode ring.

19. The active electrode of claim 17, wherein each of the second outer surface and the second inner surface of the electrode ring is provided with a scalloped design.

20. The active electrode of claim 17, wherein the second outer surface of the electrode ring is not provided with a scalloped design.

21. A method of conducting an electrosurgical procedure comprising the steps of:
providing an active electrode of an electrosurgical probe comprising a shaft having a proximal end and a distal end, the shaft being a swaged and bent one-piece metal tube; and at least one active electrode located at or near said distal end of the shaft including an electrode base and an electrode ring attached to the electrode base and surrounding the electrode base, wherein a most distal surface of the electrode base has a first scalloped configuration, and wherein a most distal surface of the electrode ring has a second scalloped configuration, and wherein the electrode base and the electrode ring are formed of an electrically conductive material;
positioning the active electrode in the proximity of a tissue to be treated in the presence of an electrically conductive fluid; and
effecting ablation of at least a portion of the tissue to be treated.

22. The method of claim 21, wherein the first scalloped configuration is a 7-face scalloped design and the second scalloped configuration is one of a 5-face, 10-face or 20-face scalloped.

23. The method of claim 21, wherein the electrode base is configured to allow suction and aspiration through it.

* * * * *